(12) United States Patent
Gandelman et al.

(10) Patent No.: US 8,481,746 B2
(45) Date of Patent: Jul. 9, 2013

(54) DIARYLPHOSPHINE-CONTAINING COMPOUNDS, PROCESSES OF PREPARING SAME AND USES THEREOF AS TRIDENTATE LIGANDS

(75) Inventors: Mark Gandelman, Kfar-Saba (IL); Elaine Melissa Schuster, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 668 days.

(21) Appl. No.: 12/465,719

(22) Filed: May 14, 2009

(65) Prior Publication Data
US 2010/0292100 A1    Nov. 18, 2010

(51) Int. Cl.
    *C07F 17/02*    (2006.01)
(52) U.S. Cl.
    USPC ............. 548/103; 548/119; 506/21; 506/15
(58) Field of Classification Search
    None
    See application file for complete search history.

(56) References Cited

FOREIGN PATENT DOCUMENTS
WO   WO 2008/145976   12/2008

OTHER PUBLICATIONS

Degl'Innocenti (1995 Tetrahedron Letters 36: 9031-9034).*
Buckler et al (1961 JACS 83:168-173).*
Schuster et al. "Synthesis of Novel Bulky, Electron-Rich Propargyl and Azidomethyl Dialkyl Phosphines and Their Use in the Preparation of Pincer Click Ligands", Organometallics, 28(17): 5025-5031, Aug. 5, 2009. Abstract.
Schuster et al. "Versatile, Selective, and Switchable Coordination Modes of Pincer Click Ligands", Organometallics, 28(24): 7001-7005, Nov. 13, 2009.
Morales-Morales "Pincer Complexes. Applications in Catalysis", Revista de la Sociedad Química de México, 48(4): 338-346, 2004.
Restriction Official Action Dated Dec. 13, 2011 From the US Patent and Trademark Office Re. U.S. Appl. No. 12/779,093.
Detz et al "'Clickphine': A Novel and Highly Versatile P,N Ligand Class Via Click Chemistry", Organic Letters, 8(15): 3227-3230, Jun. 27, 2006.
Dolhem et al "Modular Synthesis of ChiraClick Ligands: A Library of P-Chirogenic Phosphines", Journal of Combinatorial Chemistry, 9(3): 477-486, Mar. 10, 2007.
Kolb et al "Click Chemistry: Diverse Chemical Function From a Few Good Reactions", Angwandte Chemie International Edition, 40:2005-2021, 2004.
Rostovtsev et al "A Stepwise Huisgen Cycloaddition Process: Copper(I)-Catalyzed Regioselective 'Ligation' of Azides and Terminal Alkynes", Angewndte Chemie International Edition, 41(14): 2596-2599, 2002.
Schuster et al "Pincer Click Ligands", Angewandte Chemie International Edition, 47: 4555-4558, 2008.
Official Action Dated Mar. 6, 2012 From the US Patent and Trademark Office Re. U.S. Appl. No. 12/779,093.
Anteunis et al. "Triesters of Tris (Hydroxymethyl) Phosphine Oxide", Bulletin des Societes Chimique Belges, 74(11-12): 622-628, 1965, ZCAPLUS, ACS on STN, Accession No. 1966:35992, Document No. 64: 35992, 1966.
Chance et al. "Synthesis of Some Halomethylphosphine Oxides", Journal of Chemical and Engineering Data, 12(2): 282-283, 1967, ZCAPLUS, ACS on STN, Accession No. 1967:105019, Document No. 66:105019, 1967.
Grinshtein et al. "Hydroxymethylation of Phosphine and Its Derivatives", Doklady Akademii Nauk SSSR, 139: 1359-1362, 1961, ZCAPLUS, ACS on STN, Accession No. 1962:7769, Document No. 56:7769, 1962.
Grinshtein et al. "Synthesis of Organophosphorus Compounds From Phosphorus Hydrides. III. Reactions of Ethyl-, Diethyl-, and Methylethylphosphines With Paraformaldehyde", Zhurnal Obshchei Khimii, 36(2): 302-306, 1966, ZCAPLUS, ACS on STN, Accession No. 1966:93586, Document No. 64:93586, 1966.
Hoffman "Action of Hydrogen Phosphide on Formaldehyde", Journal of the American Chemical Society, 52: 2995-2998, 1930, ZCAPLUS, ACS on STN, Accession No. 1930:37243, Document No. 24:37243, 1930.
Kabachnik et al. "Pseudoallylic Rearrangements of Tris (Chloromethyl) Phosphine", Doklady Akademii Nauk SSSR, 143: 592-595, 1962, ZCAPLUS, ACS on STN, Accession No. 1962:423310, Document No. 57:23310, 1962.
Moedritzer et al. "P31 Nuclear Magnetic Resonance (NMR) Sptectra of P Compounds", Journal of Chemical and Engineering Data, 7: 307-310, 1962, ZCAPLUS, ACS on STN, Accession No. 1962:401831, Document No. 57:1831, 1962.
Petrov et al. "Preparation of Dialkylmethylolphosphines", Zhurnal Obshchei Khimii, 35(11): 2062-2065, 1965, ZCAPLUS, ACS on STN, Accession No. 1966:35984, Document No. 64: 35984, 1966.
Notice of Allowance Dated Jul. 19, 2012 From the US Patent and Trademark Office Re. U.S. Appl. No. 12/779,093.

* cited by examiner

Primary Examiner — Christopher M Gross

(57) ABSTRACT

A novel process of preparing tridentate ligands containing a diarylphosphine electron donating group are disclosed. Use of this process for preparing a combinatorial library of such tridentate ligands and of organometallic complexes containing same is also disclosed. Further disclosed are novel diarylphosphine-containing compounds that can serve as tridentate ligands (e.g., pincer ligands), combinatorial libraries of such tridentate ligands, organometallic complexes containing these ligands (e.g., pincer complexes), and combinatorial libraries of such complexes. Methods utilizing these libraries for screening for candidate organometallic catalysts are also disclosed.

25 Claims, 5 Drawing Sheets

3a: Ar = C$_6$H$_5$
3b: Ar = o-MeOC$_6$H$_4$
i: CuSO$_4$/Na Ascorbate, THF/H$_2$O, 23°C, 24h
ii: DABCO, 70°C, 5h, for 5, 6, 7. HSiCl$_3$/NEt$_3$, 120°C, 12h for 7, 8.

5,9: $D^1 = D^2 = PPh_2$
6,10: $D^1 = PPh_2$, $D^2 = $ pyridine
7, 11: $D^1 = PhS$, $D^2 = PPh_2$
8, 12: $D^1 = PhS$, $D^2 = P(o\text{-MeOC}_6H_4)_2$

DIARYLPHOSPHINE-CONTAINING COMPOUNDS, PROCESSES OF PREPARING SAME AND USES THEREOF AS TRIDENTATE LIGANDS

FIELD AND BACKGROUND OF THE INVENTION

The present invention, in some embodiments thereof, relates to novel compounds, methods of preparing same, metal complexes formed therewith and uses thereof and, more particularly, but not exclusively, to novel diarylphosphine-containing compounds that can be utilized for forming a library of tridentate ligands, such as, for example, pincer-type ligands, to methods of synthesizing these compounds and ligands, to uses thereof in, for example, the preparation of organometallic complexes and to the various uses of such organometallic complexes.

Organophosphorus compounds have enjoyed a variety of important applications in numerous actively developing fields of science and technology. Organophosphorus compounds have found use as agricultural insecticides, anti-corrosion and fire-resistant agents, extractants in hydrometallurgy and as antimicrobial and chemotherapeutic agents.

In addition, phosphorus-containing compounds have received special attention due to their spectacular applications in synthetic chemistry both as reagents and ligands for metal-based catalysis. From a synthetic point of view, phosphorus-containing precursors decorated with versatile functional groups are especially valuable, particularly if these groups can be easily interconverted and further diversified.

One of the most interesting synthetic applications of organophosphorus compounds is the formation of tridentate pincer type ligands, also referred to herein and in the art as "pincer ligands".

A pincer ligand is a type of a chelating agent that can bind tightly to three adjacent coplanar sites, usually on a transition metal. Typical tridentate pincer type ligands have the general form $D_1CD_2$, wherein C is a carbon atom that can potentially interact with a metal; and $D_1$ and $D_2$ are groups containing coordinating atoms (also referred to herein as electron donating atoms). In most pincer ligands, the carbon atom forms a part of an aryl ring, typically phenyl. The carbon atom can be replaced by other coordinating atoms such as nitrogen or sulfur, which typically form a part of a heterocyclyl such as a heteroaryl.

Many useful pincer ligands contain phosphines. Early examples of pincer ligands were anionic with a carbanion as the central donor site and flanking phosphine donors and are referred to as PCP pincers. Other pincer ligands include, for example, PNP, SCS, NCN, PCS, PCN, PNN, and NNN.

The assumed irreversibility of pincer-metal interaction confers high thermal stability to the resulting complexes. This stability is ascribed to the constrained geometry of the pincer ligand and steric shielding provided to the metal center by substituents of the coordinated donor groups.

Stoichiometric and catalytic applications of pincer complexes have been studied at an accelerating pace since the mid 1970's, especially for C—H activation.

Tridentate pincer type ligands have found spectacular employment in coordination, mechanistic, synthetic and supramolecular chemistry, along with nanoscience and the development of sensors and molecular switches. Most significantly, a realization that pincer ligands offer both a unique, highly protective environment for the coordinated metal center and opportunities to fine tune the steric and electronic metal properties has generated extensive research into the use of these complexes as catalysts [For reviews, see: J. T. Singleton, *Tetrahedron* 2003, 59, 1837; and D. Morales-Morales, *Rev. Quin. Mex.* 2004, 48, 338]. As a result, many important and challenging catalytic processes have been developed based on such systems.

It is generally accepted that the reactivity, selectivity and catalytic performance of pincer-based systems greatly relies on the characteristics of the donor groups D in the carefully selected ligand. These characteristics depend on the type of the coordinating atom, and further on the nature of its organic substituents.

Traditionally, pincer ligands are prepared by attaching electron donating atoms, or groups containing the same, to a ligand backbone.

Optimization of tailor-made catalysts therefore includes extensive experimental investigations, in which laborious ligand synthesis is often a serious bottleneck. Especially, synthesis of non-symmetrically substituted $D^1CD^2$ ligands ($D^1$ and $D^2$ are different groups) represents a considerable challenge, as their preparation usually includes series of steps and separations which commonly result in low yields.

The preparation of mono-phosphine and chiral phosphine ligand libraries, using the "click" reaction has recently been reported [Q. Dai, W. Gao, D. Liu, L. M. Kapes, X. Zhang, *J. Org. Chem.* 2006, 71, 3928; R. D. Detz, S. Heras, R. de Gelder, P. W. N. M. van Leeuwen, H. Hiemstra, J. N. H. Reek, J. H. van Maarseveen *Org. Lett.* 2006, 8, 3227; F. Dolhem, M. J. Johansson, T. Antonsson, N. Kann, *J. Comb. Chem.* 2007, 9, 477.

The "click" reaction is a name used to describe a Cu(I)-catalyzed stepwise variant of the Huisgen 1,3-dipolar cycloaddition of azides and alkynes to yield 1,2,3-triazole. This reaction is carried out under ambient conditions and with exclusive regioselectivity for the 1,4-disubstituted triazole product when mediated by catalytic amounts of Cu(I) salts [V. Rostovtsev, L. G. Green, V. V, Fokin, K. B. Sharpless, *Angew. Chem. Int. Ed.* 2002, 41, 2596; H. C. Kolb, M. Finn, K. B. Sharpless, *Angew Chem., Int. Ed.* 2001, 40, 2004.

SUMMARY OF THE INVENTION

The present inventors have now devised and successfully practiced a novel, general process for a selective and facile preparation of both symmetrically and non-symmetrically substituted tridentate ligands of the $D^1CD^2$ type, based on a triazole core and a diarylphosphine-containing moiety. The present inventors have further utilized these tridentate ligands for forming well-defined transition metal complexes and have further demonstrated the catalytic activity of the formed complexes.

The novel methodology described herein allows for efficient and facile preparation of an entirely novel family of tridentate ligands of the $D^1CD^2$ type, and can be advantageously utilized for creating combinatorial libraries of, for example, tridentate pincer ligands.

The methodology described herein is conceptually and generally depicted in FIG. 1, and is based upon the Sharpless-modified Huisgen [2+3] cycloaddition of alkynes and azides (the "click" reaction), forming triazoles, as the central building tool for ligand assembly [Huisgen, R. *Proc. Chem. Soc.* 1961, 357]. Thus, a variety of azides and alkynes decorated with a diarylphosphine donating group, as well as with other electron donating groups, are reacted to give a triazole-based pincer frame with two donor arms in 1,4-positions and a relatively acidic hydrogen that allows for metal insertion to form tridentate pincer-type complexes.

The present inventors have shown that by utilizing the "click chemistry" described herein, combinatorial synthesis of non-trivial ligands from relatively simple building blocks is effected and advantageously allows for efficient preparation and screening of a broad range of organometallic catalysts for a variety of synthetic applications.

According to an aspect of some embodiments of the invention there is provided a compound of the general Formula I:

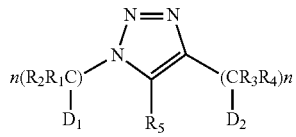

Formula I wherein:

n is an integer from 1 to 4;

$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, nitro and cyano;

$R_5$ is a leaving group capable of being dissociated so as to form a carbanion;

$D_1$ is an electron donating group of the general Formula IIa:

$$Z_1Z_2Xa \qquad \text{Formula IIa;}$$

and $D_2$ is an electron donating group of the general Formula IIb:

$$Z_3Z_4Xb \qquad \text{Formula IIb;}$$

whereas:

Xa and Xb are each independently an electron donating atom; and $Z_1$, $Z_2$, $Z_3$ and $Z_4$ are each independently absent or a substituent selected from the group consisting of substituted or non-substituted aryl, substituted or non-substituted alkyl, substituted or non-substituted alkoxy and substituted or non-substituted aryloxy, or, alternatively, at least two of $Z_1$, $Z_2$, $R_1$ and $R_2$ and/or at least two of $Z_3$, 74, $R_3$ and $R_4$ from together a five- or six-membered heteroalicyclic or heteroaromatic ring, at least one of the $D_1$ and $D_2$ having the general Formula IIa or IIb, respectively is being such that the electron donating atom is phosphorus and either the $Z_1$ and $Z_2$ or the $Z_3$ and $Z_4$ substituents of the phosphorous are each independently a substituted or non-substituted aryl.

According to some embodiments, $R_1$-$R_5$ are each hydrogen.

According to some embodiments, n equals 1.

According to some embodiments, each of the electron donating atoms Xa and Xb is independently selected from the group consisting of phosphorous, sulfur, nitrogen and carbon, the carbon being a carbene that forms a part of a N-heteroalicyclic or a N-heteroaryl.

According to some embodiments, Xa and Xb are each phosphorus.

According to some embodiments, $Z_1$ and $Z_2$ are each aryl.

According to some embodiments, $Z_1$, $Z_2$, $Z_3$ and $Z_4$ is independently a substituted or non-substituted aryl.

According to some embodiments, Xa is phosphorus and Xb is nitrogen.

According to some embodiments, Xa is sulfur and Xb is phosphorus.

According to some embodiments, $Z_3$ and $Z_4$ are each aryl.

According to some embodiments, $Z_1$ is aryl and $Z_2$ is absent.

According to some embodiments, the compound is selected from the group consisting of:

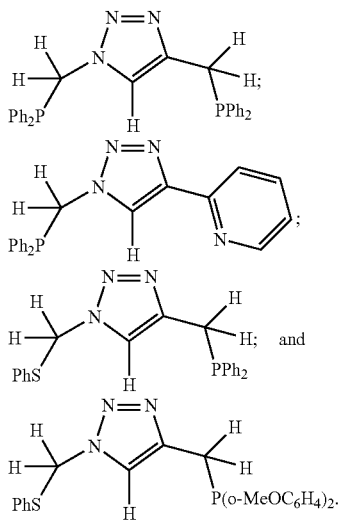

According to an aspect of some embodiments of the invention there is provided a process of preparing the compounds described herein, the process comprising:

reacting, via a 1,3-dipolar cycloaddition reaction, a compound having general Formula IIIa:

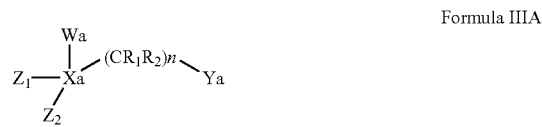

Formula IIIA with a compound having general Formula IIIb:

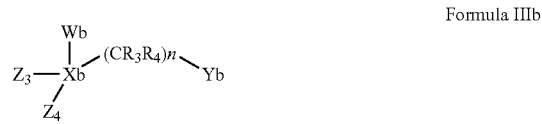

Formula IIIb wherein:

Wa and Wb are each independently a protecting group or absent;

Ya is a —$N_3$ group;

Yb is a —≡—$R_5$ group;

n is the integer from 1 to 4;

$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, halogen, nitro and cyano;

$R_5$ is the leaving group;

Xa and Xb are each independently the electron donating atom; and $Z_1$, $Z_2$, $Z_3$ and $Z_4$ are each independently absent or the substituent selected from the group consisting of substituted or non-substituted aryl, substituted or non-substituted alkyl, substituted or non-substituted alkoxy and substituted or non-substituted aryloxy, or, alternatively, at least two of $Z_1$, $Z_2$, $R_1$ and $R_2$ and/or at least two of $Z_3$, $Z_4$, $R_3$ and R from together a five- or six-membered heteroalicyclic or heteroaromatic ring, at least one of the $D_1$ and $D_2$ having the general Formula IIa or IIb, respectively, is being such that the electron donating atom is phosphorus and either the $Z_1$ and $Z_2$ in or the $Z_3$ and $Z_4$ substituents of the phosphorous are each independently a substituted or non-substituted aryl.

According to some embodiments, the cycloaddition reaction is performed in the presence of a copper (I) catalyst.

According to some embodiments, the cycloaddition reaction is performed at room temperature.

According to some embodiments, the cycloaddition reaction is the "click" reaction.

According to some embodiments, at least one of the Wa and Wb is the protecting group, the process further comprising, subsequent to the reacting: removing the protecting group.

According to some embodiments, the process is being for forming a combinatorial library of tridentate ligands having the general Formula I.

According to yet another aspect of some embodiments of the invention there is provided combinatorial library of tridentate ligands, the library comprising a plurality of compounds having the general Formula I, as described herein, the compounds being different from one another in at least one of the electron donating groups $D_1$ and $D_2$ and/or at least one of the n and $R_1$-$R_5$.

According to an additional aspect of some embodiments of the invention there is provided an organometallic complex comprising a metal and the compound described herein serving as a tridentate ligand being in complex with the metal, the complex having general Formula V:

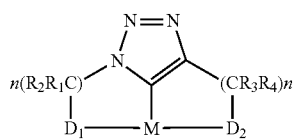

Formula V wherein:

n is the integer from 1 to 4;

$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, halogen, nitro and cyano;

M is a transition metal;

$D_1$ is the electron donating group of the general Formula IIa:

Formula IIa;

and $D_2$ is an electron donating group of the general Formula IIb:

Formula IIb, whereas:

Xa and Xb are each independently the electron donating atom; and $Z_1$, $Z_2$, $Z_3$ and $Z_4$ are each independently absent or a substituent selected from the group consisting of substituted or non-substituted aryl, substituted or non-substituted alkyl, substituted or non-substituted alkoxy and substituted or non-substituted aryloxy, or, alternatively, at least two of Zen $Z_2$, $R_1$ and $R_2$ and/or at least two of $Z_3$, $Z_4$, $R_3$ and $R_4$ from together a five- or six-membered heteroalicyclic or heteroaromatic ring, at least one of the $D_1$ and $D_2$ having the general Formula IIa or IIb, respectively, is being such that the electron donating atom is phosphorus and either the $Z_1$ and $Z_2$ or the $Z_3$ and $Z_4$ substituents of the phosphorus are each independently a substituted or non-substituted aryl.

According to some embodiments, M is selected from the group consisting of palladium, platinum, rhodium, zirconium, ruthenium, iridium, nickel, iron and osmium, each optionally further comprising an additional ligand.

According to yet an additional aspect of some embodiments of the invention there is provided a process of preparing the organometallic complex described herein, the process comprising contacting a salt or a complex of the metal with the compound described herein.

According to some embodiments, the contacting is performed under basic conditions.

According to still an additional aspect of some embodiments of the invention there is provided a combinatorial library of organometallic complexes, the library comprising a plurality of organometallic complexes having general Formula V, as described herein.

According to a further aspect of some embodiments of the invention there is provided a method of identifying a candidate organometallic complex for catalyzing a chemical reaction, the method comprising: screening the combinatorial library of organometailic complexes as described herein, by determining a catalytic activity of at least a portion of the plurality of organometallic complexes in the chemical reaction, thereby identifying the candidate organometallic complex.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to novel compounds, methods of preparing same, metal complexes formed therewith and uses thereof and, more particularly, but not exclusively, to novel diarylphosphine-containing compounds that can be utilized for forming a library of tridentate ligands, such as, for example, pincer-type ligands, to methods of synthesizing these compounds and ligands, to uses thereof in, for example, the preparation of organometallic complexes and to the various uses of such organometallic complexes.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed hereinabove, tridentate pincer type ligands have found spectacular employment in many applications, particularly in the field of organometallics. Thus, in recent years, pincer type organometallic complexes have been extensively studies. The realization that pincer ligands offer both a unique, highly protective environment for the coordinated metal center and opportunities to fine tune the steric and electronic metal properties has generated extensive research into the use of these complexes as catalysts. As a result, many important and challenging catalytic processes have been developed to based on such systems.

It is generally accepted that the reactivity, selectivity and catalytic performance of pincer-based systems relies on the characteristics of the electron donating groups in the carefully selected ligand. These characteristics depend on the type of the coordinating atom, and further on the nature of its substituents.

As mentioned hereinabove, pincer ligands are traditionally prepared by attaching electron donating atoms or groups to a ligand backbone. Such a synthetic pathway often involves a laborious process and commonly results in low yields, particularly due to the non-regioselectivity of attachment and the need to separate the desired product from its regioisomers. This is even more complicated in cases where the desired ligand is heterosymmetric (when $D_1$ and $D_2$ are different from one another).

Figure 1:
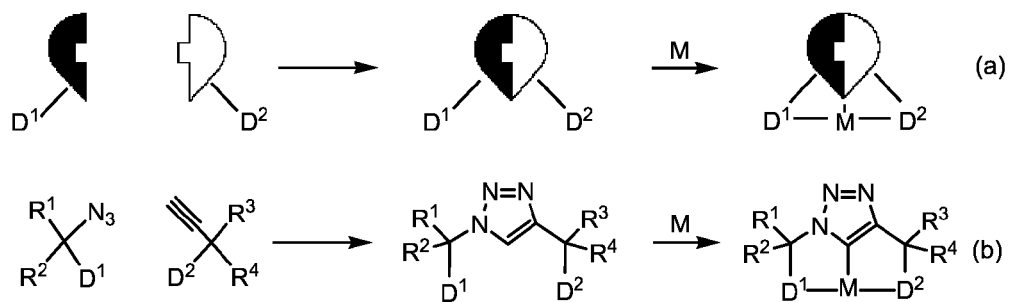
FIG. 1 presents schematic illustrations depicting the conceptual approach (a) and a generalized synthetic strategy (b) for utilizing "click" chemistry for obtaining ligands and organometallic complexes according to embodiments of the invention.

While conceiving the present invention, it was envisioned that an efficient and facile preparation of a novel family of tridentate ligands that comprise two electron donating groups could be achieved by the design and preparation of tridentate ligands which may be readily synthesized via "click" chemistry, by selective and easy complementary binding of two precursors, each comprising an electron donating group, by covalent assembly, to afford a pincer type system in which the moiety formed by the reaction of the two precursors has an ability to interact with a metal ion. This concept is schematically illustrated in FIG. 1A.

It was further envisioned that the abovementioned approach could greatly facilitate the creation of novel and diverse libraries of such tridentate ligands through combinatorial chemistry, utilizing selected precursors.

While further conceiving the present invention, it was envisioned that the Huisgen 1,3-dipolar cycloaddition of azides and alkynes to yield triazoles could be utilized for ligand assembly. It was further envisioned that the Sharpless-modified Huisgen [2+3]cycloaddition of alkynes and azides, which can be carried out under ambient conditions and with exclusive regioselectivity for the 1,4-disubstituted triazole product when mediated by catalytic amounts of Cu(I) salts, coined the "Click" reaction, can be efficiently utilized for that purpose.

It was envisioned that such a methodology would allow assembling a variety of azides and alkynes, decorated with various electron donating moieties, to give a triazole-based pincer frame with two donor arms at 1,4-positions of the triazole.

While reducing the present invention to practice, a plurality of compounds was designed according to the underlying principles outlined above, based on diarylphosphine-containing precursors, and were readily synthesized. As is demonstrated in the Examples section that follows, a "click" reaction between azide-containing precursors and alkyne-containing precursors was highly efficacious for preparing triazole compounds, regioselectively substituted with two electron donating groups. The resulting triazole-based ligands possess two coordinating "arms" in the 1,4-positions, and a relatively acidic C—H bond in between them, which is suitable for directed metal insertion (see, FIGS. 1B and 2).

Importantly, in contrast to traditional synthetic methodologies, hetero-tridentate ligands are selectively obtained Using this methodology, as only this covalent assembly is possible under "click" reaction conditions.

As further demonstrated therein, such triazole compounds are effective as tridentate pincer ligands, and hence useful in the preparation of organometallic complexes. The general reaction of azide- and alkyne-containing precursors to form a triazole, and preparation of an organometallic complex therefrom, is schematically illustrated in FIG. 1B.

Figure 2:
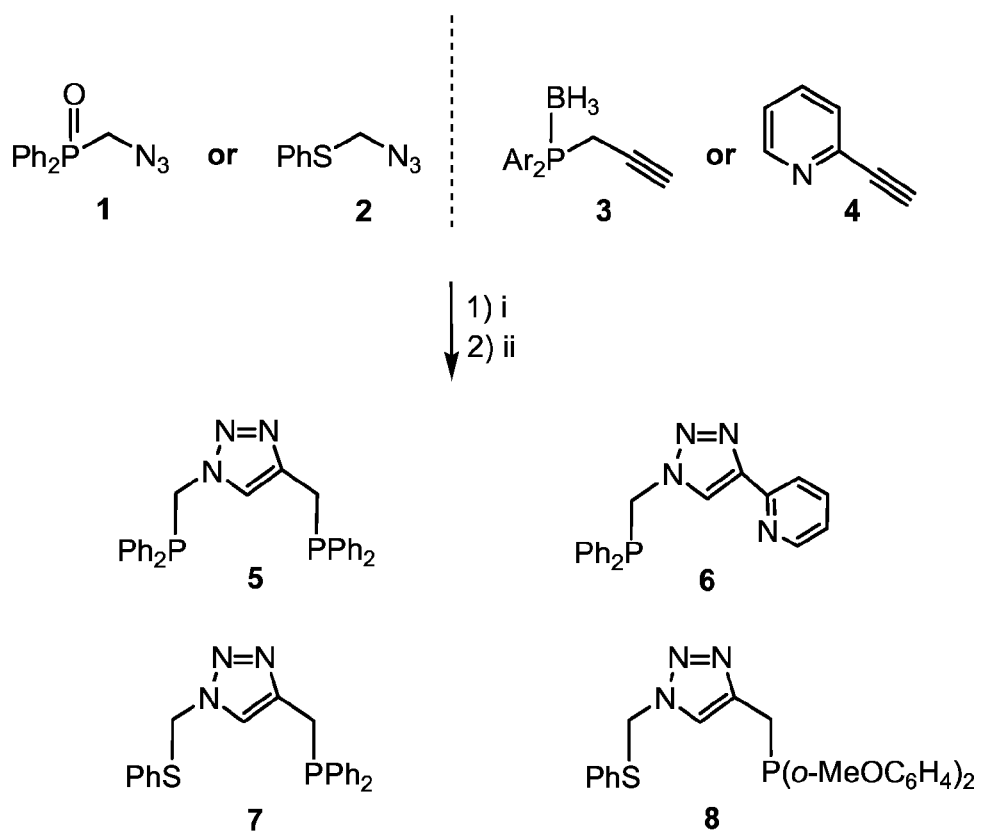
FIG. 2 presents a schematic illustration depicting the combinatorial syntheses of exemplary compounds according to embodiments of the invention.
Figure 3:
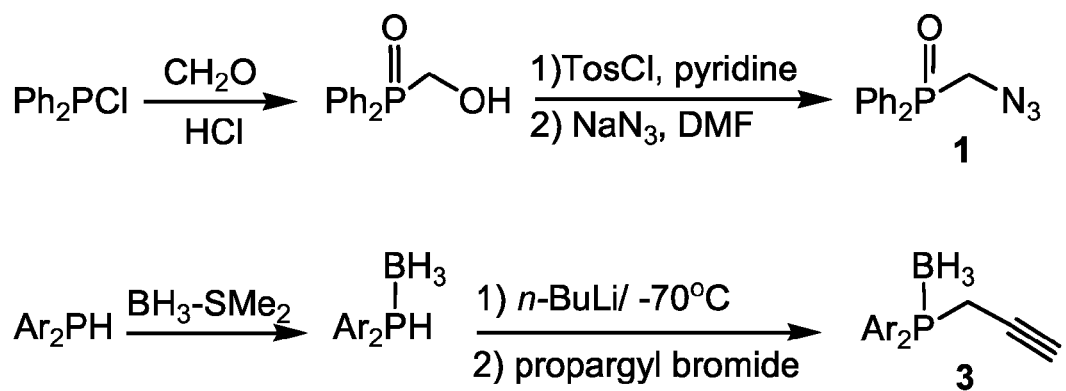
FIG. 3 presents a schematic illustration depicting the syntheses of exemplary building blocks utilized for forming the compounds according to embodiments of the invention.

As demonstrated in the Examples section that follows, because of the ease of synthesis, a variety of tridentate ligands may be readily prepared by combinatorial synthesis using various precursors. Combinatorial synthesis of exemplary compounds is depicted in FIG. 2. Synthesis of exemplary precursors is depicted in FIG. 3.

Thus, a conceptually new approach to the synthesis of tridentate ligands has been developed and demonstrated for precursor molecules bearing diarylphosphine moieties.

The methodology taught herein allows for efficient and facile preparation of an entirely novel family of tridentate ligands, and further allows the creation of tridentate ligand (e.g., pincer ligand) libraries.

This family of novel tridentate ligands is also termed herein "pincer click ligands" or "PCLs".

Figure 4:
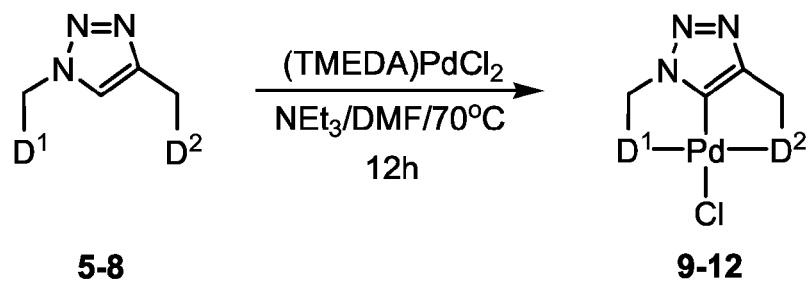
FIG. 4 presents a schematic illustration depicting the formation of exemplary palladium complexes according to embodiments of the invention.
Figure 5:
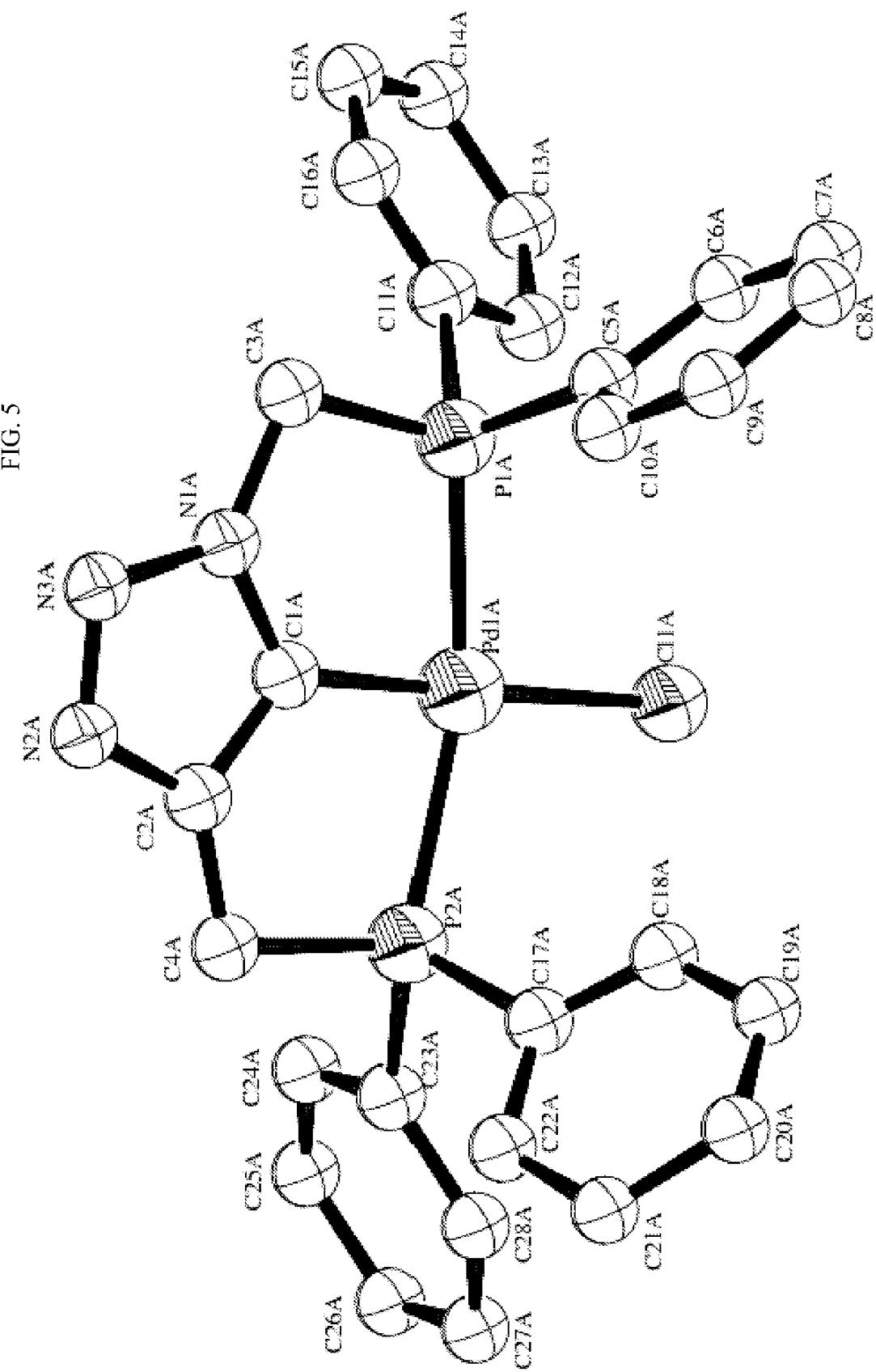
FIG. 5 presents a perspective view of a molecule of Compound 9 as determined by X-ray crystallography; hydrogen atoms are omitted for clarity; selected bond lengths [Å] and angles [°]: Pd1A-C1A 1.920(17), Pd1A-P1A 2.310(5), Pd1A-P2A 2.343(6), Pd1A-Cl1A 2.354(4), P1A-Pd1A-P2A 157.02(18), C1A-Pd1A-Cl1A 177.8(5).

The tridentate ligands may be used to form organometallic complexes, as shown in FIGS. 4 and 5.

As is further demonstrated in the Examples section that follows, well-defined transition metal complexes based on these new ligands were prepared and structurally characterized, demonstrating a tridentate mode of coordination for the newly developed compounds. These complexes were further found as highly efficient catalysts.

The novel methodology described herein was found to be highly advantageous for combinatorial synthesis of non-trivial ligands from relatively simple building blocks. It allows for efficient preparation and screening of a broad range of organometallic is catalysts for a variety of synthetic applications. Further, the use of "click" conditions ensure operationally simple and reliable reaction protocols, broad functional group tolerance, high yields and easy purification of the products. It allows a selective straightforward synthesis of tailor-made homo- and hetero-tridentate ligands exclusively, and the electron donating groups can be easily varied. Moreover, the triazole unit in the backbone of the ligand offers an interesting alternative to the traditional phenyl-based frame. It may be further functionalized, and additional metal ions could be coordinated to the nitrogen atom after the creation of the pincer complex.

Hence, according to an aspect of some embodiments of the invention there are provided novel compounds, each comprising a triazole core unit, which is substituted at positions 1 and 4 thereof by moieties that contain electron-donating groups. As discussed hereinabove, these compounds can serve as tridentate ligands, e.g., pincer ligands, being either homo-tridentate ligands (having identical electron donating groups within the 1,4-substituents) or hetero-tridentate ligands (having different electron donating groups within the 1,4-substituents).

The compounds described herein may be collectively represented by the general Formula I:

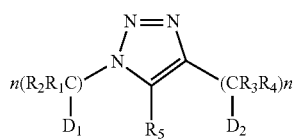

Formula I wherein:

n is an integer from 1 to 4;

$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, halogen, nitro and cyano;

$R_5$ is a leaving group that is capable of being dissociated so as to form a carbanion;

$D_1$ is an electron donating group of the general Formula IIa:

$Z_1Z_2Xa$  Formula IIa;

and $D_2$ is an electron donating group of the general Formula IIb:

$Z_3Z_4Xb$  Formula IIb;

whereas:

Xa and Xb are each independently an electron donating atom; and $Z_1$, $Z_2$, $Z_3$ and $Z_4$ are each independently absent or a substituent selected from the group consisting of substituted or non-substituted aryl, substituted or non-substituted alkyl, substituted or non-substituted alkoxy and substituted or non-substituted aryloxy, or, alternatively, at least two of $Z_1$, $Z_2$, $R_1$ and $R_2$ and/or at least two of $Z_3$, 74, $R_3$ and $R_4$ form together a five- or six-membered heteroalicyclic or heteroaromatic ring.

According to some embodiments of the invention, at least one of $D_1$ and $D_2$ having general Formula IIa or IIb, respectively, is such that the electron donating atom is phosphorus and either the $Z_1$ and $Z_2$ or the E3 and $Z_4$ substituents of the phosphorus are each independently a substituted or non-substituted aryl.

Accordingly, the compounds described herein comprise at least one electron donating group ($D_1$ and/or $D_2$ in the general Formula hereinabove), which comprises a diarylphosphine group.

As used herein, the phrase "diarylphosphine" describes a R'R"P-group, wherein R' and R" are each independently an aryl, as defined herein.

As widely described in the art, diarylphosphines serve as highly beneficial electron donating groups in pincer type tridentate ligands.

As used herein throughout, the term "alkyl" refers to a saturated or unsaturated aliphatic hydrocarbon including straight chain and branched chain groups. In some embodiments, the alkyl group has 1 to 20 carbon atoms. In some embodiments, the alkyl is a medium size alkyl having 1 to 10 carbon atoms. In some embodiments, the alkyl is a lower alkyl having 1 to 4 carbon atoms. The alkyl group may be substituted or unsubstituted. When substituted, the substituent group can be, for example, cycloalkyl, aryl, heteroaryl, heteroalicyclic, halo, hydroxy, alkoxy, aryloxy, thiohydroxy, thioalkoxy, thioaryloxy, disulfide, sulfinyl, sulfonyl, sulfonate, sulfate, cyano, nitro, phosphonyl, phosphinyl, oxo, carbonyl, thiocarbonyl, urea, thiourea, carbamyl, thiocarbamyl, amido, carboxylate, sulfonamido and amine, as these terms are defined herein. In some embodiments, the substituent is alkyl, cycloalkyl, aryl, heteroaryl, heteroalicyclic, alkoxy, thioalkoxy, hydroxy, thiol, amine, nitro and/or cyano.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted. When substituted, the substituent group can be, for example, cycloalkyl, aryl, heteroaryl, heteroalicyclic, halo, hydroxy, alkoxy, aryloxy, thiohydroxy, thioalkoxy, thioaryloxy, disulfide, sulfinyl, sulfonyl, sulfonate, sulfate, cyano, nitro, phosphonyl, phosphinyl, oxo, carbonyl, thiocarbonyl, urea, thiourea, carbamyl, thiocarbamyl, amido, carboxylate, sulfonamido and amine, as these terms are defined herein. In some embodiments, the substituent is alkyl, cycloalkyl, aryl, heteroaryl, heteroalicyclic, alkoxy, thioalkoxy, hydroxy, thiol, amine, nitro and/or cyano.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, cycloalkyl, aryl, heteroaryl, heteroalicyclic, halo, hydroxy, alkoxy, aryloxy, thiohydroxy, thioalkoxy, thioaryloxy, disulfide, sulfinyl, sulfonyl, sulfonate, sulfate, cyano, nitro, phosphonyl, phosphinyl, oxo, carbonyl, thiocarbonyl, urea, thiourea, carbamyl, thiocarbamyl, amido, carboxylate, sulfonamido and amine, as these terms are defined herein. In some embodiments, the substituent is alkyl, cycloalkyl, aryl, heteroaryl, heteroalicyclic, alkoxy, thioalkoxy, hydroxy, thiol, amine, halogen, nitro and/or cyano.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, cycloalkyl, aryl, heteroaryl, heteroalicyclic, halo, hydroxy, alkoxy, aryloxy, thiohydroxy, thioalkoxy, thioaryloxy, disulfide, sulfinyl, sulfonyl, sulfonate, sulfate, cyano, nitro, phosphonyl, phosphinyl, oxo, carbonyl, thiocarbonyl, urea, thiourea, carbamyl, thiocarbamyl, amido, carboxylate, sulfonamido and amine, as these terms are defined herein. In some embodiments, the substituent is alkyl, cycloalkyl, aryl, heteroaryl, heteroalicyclic, alkoxy, thioalkoxy, hydroxy, thiol, amine, halogen, nitro and/or cyano.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituent group can be, for example, cycloalkyl, aryl, heteroaryl, heteroalicyclic, halo, hydroxy, alkoxy, aryloxy, thiohydroxy, thioalkoxy, thioaryloxy, disulfide, sulfinyl, sulfonyl, sulfonate, sulfate, cyano, nitro, phosphonyl, phosphinyl, oxo, carbonyl, thiocarbonyl, urea, thiourea, carbamyl, thiocarbamyl, amido, carboxylate, sulfonamido and amine, as these terms are defined herein. In some embodiments, the substituent is selected from the group consisting of alkyl, cycloalkyl, aryl, heteroaryl, heteroalicyclic, alkoxy, thioalkoxy, hydroxy, thiol, amine, nitro and/or cyano. Representative examples are 4,5-dihydroimidazole, piperidine, piperazine, tetrahydrofuran, tetrahydropyran, morpholine and the like.

As used herein, the terms "amine" and "aminio" refer to a —NR'R" group, wherein R' and R" are selected from the group consisting of hydrogen and substituted or unsubstituted alkyl, cycloalkyl, heteroalicyclic (bonded through a ring carbon), aryl, and heteroaryl (bonded through a ring carbon). In some embodiments, R' and R" are each independently hydrogen or an alkyl comprising 1 to 4 carbon atoms. In some embodiments, R' and R" are each hydrogen.

A "hydroxy" group refers to an OH group.

An "azide" group refers to a —N=N$^+$=N$^-$ (—N$_3$) group.

An "alkoxyr" group refers to both —O-alkyl and —O-cycloalkyl groups.

An "aryloxy" group refers to both —O-aryl and —O-heteroaryl groups.

A "thiohydroxy" group or "thiol" refers to a —SH group.

A "thioalkoxy" group refers to both S-alkyl and —S-cycloalkyl groups.

A "thioaryloxy" group refers to both —S-aryl and —S-heteroaryl groups.

A "disulfide" group refers to both a —S-thioalkoxy and a —S-thioaryloxy group.

A "carbonyl" group refers to a —C(=O)—R' group, where R' is defined as hereinabove.

A "thiocarbonyl" group refers to a —C(=S)—R' group, where R' is as defined herein.

An "oxo" group refers to a =O group.

A "carboxylate" encompasses both —C(=O)—O—R' and R'C(=O)—O— groups, where R' is as defined herein.

A "thiocarboxy" or "thiocarboxylate" group refers to both —C(=S)—O—R' and —O—C(=S)R' groups, where R' is as defined herein.

A "halo" or "halogen" group refers to fluorine, chlorine, bromine or iodine.

A "sulfinyl" group refers to an —S(=O)—R' group, where R' is as defined herein.

A "sulfonyl" group refers to an —S(=O)$_2$—R' group, where R' is as defined herein.

A "sulfonate" group refers to an —S(=O)$_2$—O—R' group, where R' is as defined herein.

A "sulfate" group refers to an O—S(=O)$_2$—O—R' group, where R' is as defined as herein.

A "sulfonamide" or "sulfonamido" group encompasses both —S(=O)$_2$—NR'R" and R'S(=O)$_2$—N(R')-groups, where R' and K" are as defined herein.

A "carbamyl" or "carbamate" group encompasses —OC(=O)—NR'R" and R'OC(=O)—NR"-groups, where R' and R' are as defined herein.

A "thiocarbamyl" or "thiocarbamate" group encompasses —OC(=S)—NR'R" and R'OC(=S)—NR"-groups, where R' and R" are as defined herein.

An "aride" or "amido" group encompasses C(=O)—NR'R" and R'C(=O)—NR"-groups, where R' and R" are as defined herein.

A "urea" group refers to an —N(R')—C(=O)—NR"R'" group, where each of R' and R" is as defined herein, and R'" is defined as R' and R" are defined herein.

A "nitro" group refers to an —NO$_2$ group.

A "cyano" group refers to a —CMN group.

The term "phosphonyl" or "phosphonate" describes a —P(=O)(OR')(OR") group, with R' and R" as defined hereinabove.

The term "phosphate" describes an —O—P(=O)(OR')(OR") group, with each of R' and R" as defined hereinabove.

The terms "phosphinyl" and "phosphine" describe a —PR'R" group, with each of R' and R" as defined hereinabove.

The term "phosphine oxide" describes a —P(=O)R'R" group, where R' and K" are as defined herein.

The term "thiourea" describes a —N(R')—C(=S)—NR"RR'" group, with each of R', R" and R'" as defined hereinabove.

The term "alkene" refers to an alkyl, as defined herein, which comprises at least two carbon atoms, and at least one carbon-carbon double bond.

The term "alkyne" or "alkynyl" refers to an alkyl, as defined herein, which comprises at least two carbon atoms, and at least one carbon-carbon triple bond.

An example of alkyne is propargyl, which comprises 3 carbon atoms and one triple bond. In some embodiments, where n in the general Formula I herein is 1, the compounds is made by assembling an azide and a propargyl.

As used herein, the phrase "electron donating group" describes a chemical group that comprises at least one electron donating atom, as this phrase is defined herein. This phrase is also referred to herein interchangeably as "donor"[1], "donor group" and "coordinating group".

As used herein, the phrase "electron donating atom" describes any atom in a chemical group which is capable of donating one or more electrons to an electron acceptor (e.g., a metal ion), so as to coordinatively interact with the acceptor. Typically, the electron donating atom is characterized by the presence of a free electron pair. Various heteroatoms (e.g., phosphorus, sulfur, nitrogen) are known in the art to be capable of acting as electron donating atoms. In addition, a carbon atom in an N-heterocyclic carbenes may be a suitable electron donating atom.

As used herein, the term "carbene" describes any compound or group that contains a carbon atom characterized as having only two valence bonds, as well as a free electron pair. Such a carbon atom is also described herein as a "carbene carbon" or an "electron donating atom".

As used herein, the phrase "N-heterocyclic carbene" describes a carbene in which the carbene carbon is covalently bound to at least one nitrogen atom that forms a part of a heterocyclic group. Typically, the carbene carbon is covalently bound to two heteroatoms (e.g., two nitrogen atoms), which affords a relatively stable carbene. Such carbenes include, without limitation, imidazol-2-ylidenes, 1,2,4-triazol-5-ylidenes and thiazol-2-ylidenes.

As used herein, the term "heterocyclic" encompasses heteroalicyclic and heteroaryl, as these terms are defined herein.

The electron donating capability of an electron donating atom can be manipulated by the nature of its substituents or of substituents of adjacent atoms. Substituents that exhibit an electron inductive effect therefore enhance the electron donating functionality of the electron donating group.

The $D_1$ and $D_2$ groups can be the same or different. Thus, the resulting tridentate ligand are therefore homo-tridentate ligands and hetero-tridentate ligands, respectively.

The homo-tridentate ligands, according to embodiments of the invention, include two identical diarylphosphine groups as $D_1$ and $D_2$. Hetero-tridentate ligands include a diarylphosphine group as one of $D_1$ and $D_2$, and a different group, being a different diarylphosphine group or a different electron donating group, as the other one in $D_1$ and $D_2$.

Exemplary electron donating groups other than diarylphosphines include, but are not limited to, amine, N- and S-containing heteroalicyclic, N- and S-containing heteroaryls, thioalkoxy, thioaryloxy and N-heterocyclic carbenes, as defined herein.

Hetero-tridentate ligands according to embodiments of the invention can include also compounds having general Formula I above, in which $D_1$ and $D_2$ are the same or different, while the moieties linking these groups to the triazole core are different from one another.

These moieties are represented as $(CR_1R_2)n$ and $(CR_3R_4)n$ in general Formula I hereinabove.

It is to be appreciated that the integer n for the $(CR_1R_2)n$ unit and the integer n for the $(CR_3R_4)n$ unit may be the same or different f.

It is to be further appreciated that when n is greater than 1, each carbon atom of the $(CR_1R_2)n$ and/or $(CR_3R_4)n$ units is attached to a $R_1$ and $R_2$ or $R_3$ and $R_4$ substituent, respectively, whereby each of the $(CR_1R_2)n$ and $(CR_3R_4)n$ unit can be the same of be different from one another.

In some embodiments, $(CR_1R_2)n$ and $(CR_3R_4)n$ are the same in length, such that n in both units is the same.

As delineated hereinabove, each of $R_1$, $R_2$, $R_3$ and $R_4$ can be independently hydrogen, alkyl, cycloalkyl, aryl, heteroaryl, heteroalicyclic, alkoxy, thioalkoxy, hydroxy, thiol, amine, halogen, nitro or cyano.

In some embodiments, each of $R_1$, $R_2$, $R_3$ and $R_4$ is hydrogen.

In some embodiments, one or more of $R_1$, $R_2$, $R_3$ and $R_4$ is other than hydrogen.

In some embodiments, the $R_1$, $R_2$, $R_3$ and/or $R_4$ substituent is an electron donating group, such that it contributes to the electro donating functionality of the $D_1$ and/or $D_2$ electron donating groups.

In some embodiments, n equals 1. Without being bound to any particular theory, it is assumed that compounds in which n equals 1 exhibit good coordinative performance when used as tridentate ligands for complexing transition metals. Such compounds exhibit high stability that is at least partially attributed to the 5-membered heterocyclic ring(s) formed, which is more pronounced with electron donating atoms such as phosphorus (as compared, for example, to electron donating atoms such as sulfur and nitrogen). However, lengthier units can further exhibit such a coordinative performance, or can beneficially serve for other applications, and hence, n in each of the $(CR_1R_2)n$ and $(CR_3R_4)n$ units can be independently 2, 3, 4 and even higher.

According to exemplary embodiments of the present invention, n equals 1, such that $(CR_1R_2)n$ and $(CR_3R_4)n$ are each a substituted or non-substituted methylene group (e.g., $CH_2$).

In some embodiments, n equals 1 and $(CR_1R_2)n$ and $(CR_3R_4)n$ are each a —$CH_2$-group.

$R_5$ is a leaving group. The phrase "leaving group" is used in the context of embodiments of the invention to describe a chemical group or atom that is capable of being dissociated from the compound, to thereby form a carbanion.

In some embodiments, $R_5$ is hydrogen. Being at position 5 of the triazole core, this hydrogen is acidic and readily dissociates as a proton, to thereby form a carbanion.

Turning back now to the electron donating groups, it is to be understood that for each electron donating group, $Z_1$ or $Z_2$ can form a bond together with one of $R_1$ and $R_2$, or, alternatively or in addition, $Z_3$ or $Z_4$ can form a bond together with one of $R_3$ and $R_4$, such that the Xa and/or Xb electron donating atoms are linked to the adjacent carbon via a double bond.

Alternatively, or in addition, $Z_1$ or $Z_2$ can form, together with one of $R_1$ and $R_2$, or, alternatively or in addition, $Z_3$ or $Z_4$ can form together with one of $R_3$ and $R_4$, a heteroalicyclic or heteroaromatic (heteroaryl) ring.

In an example, Xa is N, $Z_3$ and $R_3$ form together a bond, such that the nitrogen is linked to the adjacent carbon via a double bond, and $Z_4$ and $R_4$ from together a =CH—CH=CH—CH= group, thus forming, e.g., a pyridin-2-yl group.

Similarly, the electron donating group formed from at least two of $R_1$, $R_2$, $Z_1$ and $Z_2$, and/or between $R_3$, $R_4$, $Z_3$ and $Z_4$, can be piperidin-2-yl, piperazin-2-yl, pyrrolidin-2-yl, tetrahydrothioplhen-2-yl, tetrahydropyrane-2-yl and thiophene-2-yl.

In some embodiments, $Z_1$ and $Z_2$a and/or $Z_3$ and $Z_4$ can form together a 5- or 6-membered heteroalicyclic or heteroaromatic ring.

According to an exemplary embodiment, Xa and Xb are each phosphorus. In some embodiments, each of $Z_1$, $Z_2$, $Z_3$ and $Z_4$ is independently a substituted or non-substituted aryl.

According to another exemplary embodiment, Xa is phosphorus and Xb is nitrogen. The phosphorus atom is bound to two aryl groups, such that $Z_1$ and $Z_2$ are each aryl. In some embodiments, the nitrogen atom forms a part of a pyridinyl group.

According to yet another exemplary embodiment, Xa is sulfur and Xb is phosphorus. In some embodiments, the sulfur atom is bound to an aryl, such that Z, is aryl and $Z_2$ is absent. The phosphorus atom is bound to two aryl groups, such that $Z_3$ and $Z_4$ are each aryl.

Exemplary compounds include:

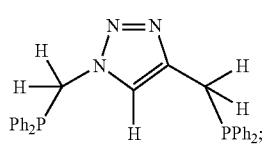

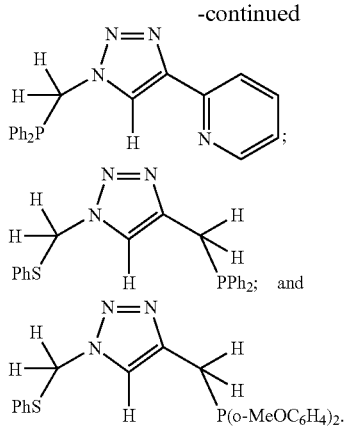

As discussed hereinabove and is exemplified hereinbelow, the compounds represented by general Formula I may be conveniently prepared from precursor molecules using a cycloaddition reaction (e.g., the "click" reaction).

Hence, according to another aspect of the present invention, there is provided a process of preparing a compound having general Formula I as described hereinabove, the process comprising reacting, via a 1,3-dipolar cycloaddition reaction, a compound having general Formula IIIa:

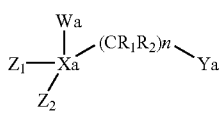

Formula IIIa with a compound having general Formula IJIb:

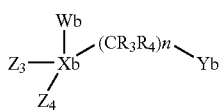

Formula IIIb wherein:

Wa and Wb are each independently a protecting group or absent;

Ya is a —$N_3$ group;

Yb is a ═══$R_5$ group;

n is an integer from 1 to 4, as described herein;

$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, halogen, nitro and cyano, as described herein;

$R_5$ is a leaving group, as described herein;

Xa and Xb are each independently an electron donating atom, as described herein; and $Z_1$, $Z_2$, $Z_3$ and $Z_4$ are each independently absent or a substituent as described herein, such that at least one of the electron donating atoms is phosphor and the $Z_1$ and $Z_2$ or $Z_3$ and $Z_4$ substituents are each independently a substituted or non-substituted aryl, as described herein.

As used herein, and is well-known in the art, a 1,3-dipolar cycloaddition reaction is a 2+3 cycloaddition reaction that results in a 5-membered ring and is facilitated by the presence of partial positive and negative charges at the 1 and 3 positions of a substance to which cycloaddition made.

As delineated hereinabove, in some embodiments, this reaction is performed according to the "click" chemistry, via a reaction coined the "click" reaction. The currently known "click" reaction is performed between an azide and an alkyne, represented by Ya and Yb, respectively, to thereby form a triazole.

It is noted that other functional groups can be utilized in the methodology described herein, as long as these functional groups, Ya and Yb, are compatible with each other in a "click" chemistry.

As further discussed hereinabove, the process described herein is advantageously performed in the presence of a copper catalyst, such as a copper (I) catalyst, which allows performing the reaction at ambient temperatures and in high yield and regioselectivity. When using a copper catalyst, the compound of Formula IIIb is selected such that $R_5$ is hydrogen.

Thus, in some embodiments, the cycloaddition reaction is performed at room temperature. As is well known in the art, the ability to perform reactions at room temperature provides considerable advantages, such as convenience and ease of synthesis, reduction of undesired reactions which compete with the cycloaddition reaction, and avoidance of heat-related damage to the precursors and/or product which may reduce yields. Performing a reaction at room temperature is particularly advantageous when one of the reactants is an azide, which is considered heat-sensitive.

As further delineated hereinabove, the starting materials (precursors) utilized in the process described herein, represented by Formulas IIIa and IIIb, can be tailor-made according to the desired properties of the final products. These starting materials are azides and alkynes, each decorated by various substituents, at least one being an electron donating group, as described herein.

The starting materials utilized in this process can be prepared as desired via well-known procedures. Some starting materials having Formulas IIIa and IIIb are commercially available. By selecting the Xa, $R_1$, $R_2$, n, $Z_1$ and $Z_2$ of the azide-containing starting material, and similarly, the Xb, $R_3$, $R_4$, n, $Z_3$ and $Z_4$ of the alkyne-containing starting material, the structural and chemical properties of the resulting tridentate ligand can be readily manipulated.

The Xa, $R_1$, $R_2$, n, $Z_1$ and $Z_2$ of the azide-containing starting material, and the Xb, $R_3$, F4, n, $Z_3$ and $Z_4$ of the alkyne-containing starting material are selected so as not to interfere with the cycloaddition reaction and to remain stable under the conditions the cycloaddition reaction is performed. Selecting the appropriate electron-donating atoms and substituents is well within the knowledge of those skilled in the art.

The electron donating group utilized in each of the precursors (starting materials), can be protected during the reaction by means of Wa and Wb protecting groups.

In some embodiments, at least one of Wa and Wb is present as a protecting group. Exemplary protecting groups include borane (e.g., $BH_3$) and oxo (i.e., ═O). Such protecting groups are particularly useful when attached to an electron donating atom (e.g., Xa or Xb) that is phosphorus, thereby forming a phosphine-borane complex or a phosphine oxide, respectively.

The protecting group may be any group which is capable of preventing or limiting a reaction involving the electron donating atom under the reaction conditions of the cycloaddition reaction, and which may be readily removed following cycloaddition. Thus, for example, phosphine-borane complexes and phosphine oxides both prevent an undesirable Staudinlger reaction between the azide and the phosphine. The phosphine can then be deprotected, for example, by DABCO (diazabicyclo[2.2.2]octane) in the case of the phosphine-borane complex, and by reduction (e.g., with trichlorosilane) in the case of the phosphine oxide, to thereby obtain a phosphine product with high yields (e.g., about 80%).

The process described herein has numerous important advantages. The conditions of the cycloaddition reaction (e.g., the "click" reaction) allow operationally simple and reliable reaction protocols, broad functional group tolerance, high yields, and easy purification of the product. In addition, the process allows selective and straightforward synthesis of tailor-made hetero-tridentate ligands (i.e., ligands wherein $D_1$ and $D_2$ are not identical) wherein the location of the attachment of each electron donating group to the triazole moiety is readily determined, and the identity of the electron donating groups may be easily varied.

Furthermore, as discussed hereinabove, compounds having Formulas IIIa and IIIb are typically either commercially available or may be prepared in a simple manner by synthetically short protocols which are well within the capabilities of one of ordinary skill in the art. Preparation of representative PCP (phosphorus-based electron donating groups), PCN (phosphorus-nitrogen-based electron donating groups) and PCS (phosphorus-sulfur-based electron donating groups) tridentate ligands are exemplified in the Examples section hereinbelow.

As exemplified in the Examples section that follows, a number of azido- and alkynyl-based starting materials were prepared and smoothly underwent copper(I)-catalyzed reciprocal [2+3] cycloaddition reactions under "click" conditions. Representative examples of the prepared ligands include PCP (Phosphorous-Phosphorous based, Compound 5), PCN (Phosphorous-Nitrogen based, Compound 6) and PCS (Phosphorous-Sulfur based, Compounds 7 and 8) binding modes (see, FIG. 2).

A typical reaction takes place in a polar solvent such as a THF/water solution, without air exclusion to furnish full conversion of the starting materials to the (optionally protected) ligands after stirring for 24 hours at room temperature.

Using the advantageous process described herein, a myriad of diverse tridentate ligands can be prepared. Application of the process described herein in a systemic combinatorial manner therefore results in a wide variety of triazole-based tridentate ligands such as, for example, pincer ligands. Thus, for example, from N(a) precursor compounds having Formula IIIa, and N(b) precursor compounds having Formula IIIb, as many as N(a)×N(b) compounds of Formula I may be prepared.

Hence, according to some embodiments, the process described herein is utilized for forming a combinatorial library of tridentate ligands having general Formula I. The ligands of the library are distinct from one another, being different in at least one of the variables $D_1$, $D_2$ and/or at least one of the variables n and $R_1$-$R_5$.

Hence, according to an aspect of embodiments of the invention, there is provided a combinatorial library of tridentate ligands having general Formula I as described herein. Such a combinatorial library comprises, for example, compounds having Formula I as described herein, which differ one from another by the nature of one or more of the electron donating group, e.g., one or more of the electron donating atoms and/or one or more of the substituents of the electron donating atoms; and/or by the nature of the units linking the electron donating group to the triazole core, e.g., the length of one or more of these units, the substituents of the carbon atoms composing this units, etc.

Such a combinatorial library can be utilized for forming a myriad of diverse organometallic complexes containing such ligands and screening these complexes for a candidate catalyst for a particular reaction, as a non-limiting example.

The compounds described herein are designed capable of forming an organometallic complex with various transition metals, due to the presence of a leaving group at the $5^{th}$ position of the triazole core. The carbon atom at the 5-position of the triazole moiety comprised by the compounds described herein becomes a carbanion relatively easily, and is located between the two electron donating groups, and is therefore particularly suitable for direct metal insertion to form, for example, a pincer metal complex.

Hence, according to another aspect of some embodiments of the present invention, there is provided an organometallic complex comprising a metal and a compound having Formula I, as described herein, wherein the compound serves as a tridentate ligand being in complex with the metal. Such organometallic complexes represent pincer type complexes, which are also referred to herein as metal pincer complexes, or simply as pincer complexes.

The organometallic complexes described herein can be collectively represented by the general Formula V:

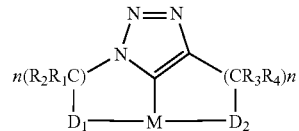

Formula V wherein:

n is an integer from 1 to 4, as described herein;

$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, halogen, nitro and cyano, as defined herein;

M is a transition metal, as described herein; and $D_1$ and $D_2$ are each an electron donating group as described herein.

It is to be understood that "M" in the general Formula V encompasses both metal atoms and metal atoms bound to one or more additional ligands (e.g., a halogen).

As used herein, and is well known in the art, the phrase "transition metal" describes an element whose atom has an incomplete d sub-shell, or which can give rise to cations with an incomplete d sub-shell (see, IUPAC definition).

Any transition metal or a complex thereof that is commonly utilized in pincer complexes is encompassed by the variable "M". These typically include late transition metals, such as those of Groups 7, 8, 9, 10 and 11. Non-limiting examples include palladium, platinum, rhodium, ruthenium, iridium, nickel, cobalt, iron, osmium and the like.

As discussed herein, the tridentate ligands described hereinabove are particularly suitable for binding to a metal so as to form a complex. Complexing of the metal by the tridentate ligand may be easily performed, as exemplified in the Examples section hereinbelow, to yield a stable organometallic complex.

Hence, according to another aspect of the present invention, there is provided a process of preparing the organometallic complex described hereinabove, comprising contacting a salt and/or a complex of the metal with the compound having Formula I, as described hereinabove. In some embodiments, the contacting is performed under basic conditions, so as to facilitate metal insertion upon removal of the acidic hydrogen at position 5 of the triazole.

Exemplary process are described in detail in the Examples section that follows.

Optionally, the process described herein can further comprise, subsequent to reacting the tridentate ligand and the metal or its salt or complex, additional attachment(s) or modification(s) of substituents that do not participate directly in the formed complex, as long as the complex remains stable under the reaction conditions. These include, for example, modification of the triazole core, modification of any of the $R_1$-$R_4$ substituents in general Formula V, modification of any of the $Z_1$-$Z_4$ substituents (e.g., modifying a substituent in the aryl moiety), and the like.

As discussed hereinabove, a combinatorial library of tridentate ligands may be prepared according to embodiments of the present invention. This library can be used to form a combinatorial library of organometallic complexes containing these ligands.

Hence, in some embodiments, there is provided a combinatorial library of organometallic complexes having the above Formula V. The organometallic complexes of the library are distinct from one another, being different in at least one of the coordinated metal (the variable "M", as defined herein), the variables $D_1$, $D_2$ and/or at least one of the variables n and $R_1$-$R_5$.

As discussed hereinabove, many organometallic complexes, and particularly complexes having a pincer structure, are useful for various purposes, for example, as catalysts for any of a wide variety of chemical (organic) reactions. However, finding an optimal catalyst may require examining the properties of a large number of organometallic complexes. Facile combinatorial access to a novel family of tridentate ligands and their corresponding metal complexes opens the door to rapid and convenient screening of these complexes in various catalytic transformations, as exemplified in the Examples section with palladium complexes with respect to catalysis of the Heck reaction.

Hence, according to another aspect of some embodiments of the invention there is provided a method of identifying a candidate organometallic complex for catalyzing a chemical (organic) reaction. The method, according to this aspect of the invention, is effected by screening the abovementioned library of organometallic complexes, by means of determining a catalytic activity of the organometallic complexes in the organic reaction, thereby identifying the candidate organometallic complex. Optionally, a candidate is identified by selecting a target catalytic activity and identifying a complex having a catalytic activity of at least the target activity. In some embodiments, more than one candidate complex is identified.

As used herein, the term "catalyzing" describes a function of promoting a chemical reaction which otherwise is very slow, does not occur or occurs at substantially low conversion rate and/or yield. Catalyzing a chemical reaction can be effected in the presence of a catalytic or stoichiometric amount of the complex.

Similarly, the phrase "catalytic activity" is used to describe an activity in promoting a chemical reaction, either catalytic or stoichiometric.

Determining a catalytic activity of organometallic complexes is well within the capabilities of those skilled in the art, and can be effected, for example, by determining the turnover number (TON) in a reaction. The complex or complexes that exhibit the highest turnover number in the selected chemical reaction is identified as a candidate catalyst for performing this reaction.

Many chemical reactions have been shown to efficiently utilize pincer type complexes. These include, for example, Heck reaction (using palladium complexes), Suzuki-Miyaura couplings (using, for example, palladium complexes), dehydrogenation of alkanes (using, for example, iridium complexes), hydrogen transfer reactions (using, for example, ruthenium complexes), aldolic condensation (using, for example, platinum or palladium complexes), asymmetric allylic alkylation (using, for example, palladium complexes), and catalytic dehydrogenation of amines and alcohols.

Other applications of the compounds and complexes described herein include cyclopropanation of alkenes, dehydrogenative esterification, and amidation.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Materials:

Bis(phenyl)(prop-2-ynyl)phosphine borane complex (Compound 3a) was prepared as described in Detz et al. [*Org. Lett.* 2006, 8, 3227].

Tetramethylethylenediamine(TMEDA)-$PdCl_2$ was prepared as described in De Graaf et al. [*Organometallics* 1989, 8, 2907].

General Methods:

Oxygen- and moisture-sensitive reactions were carried out under an atmosphere of purified nitrogen in a glove-box equipped with an inert gas purifier, or by using standard Schlenk techniques.

Dry triethylamine was obtained by distillation from $CaH_2$.

Solvents were purified by passing through a column of activated alumina under an inert atmosphere.

All commercially available reagents were used as received, unless indicated otherwise.

Analytical thin layer chromatography (TLC) was performed on pre-coated silica gel 60 F-254 plates (particle size 0.040-0.055 mm, 230-400 mesh) and visualization was accomplished using UV light or by staining with basic $KmnO_4$ dye.

NMR spectra were recorded at 300 MHz/75 MHz ($^1H/^{13}C$ NMR) in $CDCl_3$ unless otherwise stated on a Bruker AVANCE 300 MHz spectrometer at 23° C. Chemical shifts ($\delta$) are reported in parts per million and the residual solvent peak was used as an internal standard ($CDCl_3$: $\delta$ 7.261/77.0, 1H/13C NMR). $^{31}P$ NMR signals are in ppm and referenced to external 85%, $H_3PO_4$. Data are reported as follows: chemical shift, multiplicity (s=singlet, d=doublet, t=triplet, q=quartet, p=pentet, m=multiplet, b=broad), integration, and coupling constant(s) (Hz).

Example 1

Synthesis of Azide Derivatives of Diarylphosphines

Synthesis of Azidomethyl Diphenylphosphine Oxide (Compound 1):

The synthesis of Compound 1 is depicted in FIG. 3.

Synthesis of Hydroxymethyl Diphenylphosphine Oxide:

Hydroxymethyl diphenylphosphine oxide was prepared according to Lawrence & Jackson [*J. Chem. Soc., Perkin Trans.* 2002, 1, 2260]. To a mixture of HCl (18.9 ml) and aqueous formaldehyde (18.9 ml, 37 wt %) was added diphenyl chlorophosphine (2.80 ml, 10.6 mmol). The reaction mixture was heated to 100° C. for 18 hours under a nitrogen atmosphere. The reaction was neutralized with aqueous $NaHCO_3$, and the aqueous phase was extracted with $CH_2Cl_2$ (3×30 ml). The organic phase was dried with anhydrous $Na_2SO_4$. Hydroxymethyl diphenylphosphine oxide (2.907 g, 89% yield) was obtained after evaporation of the solvent as a colorless oil.

$^1H$ NMR ($CDCl_3$) $\delta$: 7.71-7.36 (m, 10H, Ar), 6.16 (s, 1H), 4.34 (d, 2H, J=2.1 Hz).

$^{13}C$ NMR ($CDCl_3$) $\delta$: 133.9 (d, $J_{CP}$=2.6 Hz), 133.2 (d, $J_{CP}$=9.2 Hz), 132.3 (d, $J_{CP}$=97 Hz), 130.4 (d, $J_{CP}$=11.6 Hz), 62.9 (d, $J_{CP}$=75 Hz).

$^{31}P$ NMR (202 MHz) $\delta$: 28.6.

Synthesis of Azidomethyl Diphenylphosphine Oxide:

This compound was prepared according to the procedure described by Detz et al. [*Org. Lett.* 2006, 8, 3227], with modification. To 50 ml of freshly distilled pyridine was added hydroxymethyl diphenylphosphine oxide (2.907 grains, 12.5 mmol) and freshly recrystallized toluene sulfonyl chloride (2.862 grams, 15 mmol). The obtained mixture was stirred at room temperature for 18 hours under a nitrogen atmosphere. The mixture was then diluted with $CH_2Cl_2$ (50 ml) and washed with $H_2O$ (3×50 ml). The solvent was evaporated, and the obtained residue was then re-dissolved in anhydrous dimethyl formamide (30 ml). To this mixture was added sodium azide (2.031 grams, 31.25 mmol). The reaction mixture was heated to 110° C. for 5 hours under a nitrogen atmosphere. The reaction was quenched with water, and was extracted with $CH_2Cl_2$ (3×50 ml). The organic phase was dried with anhydrous $Na_2SO_4$. The product was purified on silica, using ethyl acetate as eluent, to give the product (1.53 gram, 51% yield) as a white powder.

$^1H$ NMR ($CDCl_3$) $\delta$: 7.78-749 (m, 10H), 3.98 (d, 2H, $J_{HP}$=7.5 Hz, $CH_2$).

$^{13}C$ NMR ($CDCl_3$) $\delta$: 132.6 (d, $J_{CP}$=2.7 Hz), 131.2 (d, $J_{CP}$=9.6), 130.0 (d, $J_{CP}$=101 Hz), 128.8 (d, $J_{CP}$=12.0 Hz), 49.5 (d, $J_{CP}$=76.5 Hz).

$^{31}P$ NMR $\delta$: 28.8.

B. Synthesis of Azidomethyl Phenyl Sulfide (Compound 2):

The structure of Compound 2 is presented in FIG. 2.

To 5.3 ml of freshly distilled acetonitrile was added chloromethyl phenyl sulfide (1.0 gram, 6.303 mmol), sodium azide (614 mg, 9.45 mmol) and crown ether-5 (0.250 ml, 1.261 mmol). The solution was stirred for 48 hours under a nitrogen atmosphere and 10 ml water were thereafter added thereto. The aqueous phase was extracted with $CH_2Cl_2$ (3×10 ml) and the combined organic layers were washed with water (15 ml) and brine (15 ml). The organic phase was dried with anhydrous $Na_2SO_4$. The product (994 mg, 95% yield) was obtained after evaporation of the solvent as a pale yellow oil.

$^1H$ NMR ($CDCl_3$) $\delta$: 7.50-7.47 (m, 2H), 7.34-7.30 (m, 3H), 4.52 (s, 2H, $CH_2$).

$^{13}C$ NMR ($CDCl_3$) $\delta$: 131.5, 129.6, 128.1, 56.3 ($CH_2$).

Example 2

Synthesis of Alkyne Derivative of Diarylphosphines

The synthesis of alkyne derivatives of diarylphosphines is depicted in FIG. 3.

Synthesis of bis(2-methoxyphenyl)(prop-2-ynyl)phosphine borane complex (Compound 3b):

Bis(2-methoxyphenyl)phosphine borane complex was prepared as described in according to Busacca & Senanayake [*Org. Lett.* 2005, 7, 4277]. To a solution of the bis(2-methoxyphenyl)phosphine borane complex (110 mg, 0.423 mmol) in tetrahydrofuran (2 ml), n-butyl lithium (1.6 M in hexane, 265 µl, 0.423 mmol) was added at −78° C. under argon atmosphere. The solution was stirred for 15 minutes and propargylbromide (80% in toluene, 110 µL, 0.465 mmol) was then added, quenching the phosphine anion at −78° C. After 15 minutes, water was added and the solution was warmed to room temperature. The aqueous phase was extracted with ethyl acetate (3×10 ml) and the combined organic layers were washed with water (20 ml) and brine (20 ml). The organic phase was dried with anhydrous Na2SO4. The product (87 mg, 69% yield) was obtained after evaporation of the solvent as a pale yellow oil.

$^1$H NMR (CDCl$_3$) δ: 7.56-7.44 (m, 4H), 6.98-6.90 (m, 4H), 3.73 (s, 6H, O—CH$_3$) 3.51-3.45 (dd, 2H, J$_{HH}$=2.7 Hz, J$_{HP}$=13.7 Hz, CH$_2$), 1.85 (dt, 1H, J$_{HH}$=2.7 Hz, J$_{HP}$=5.7 Hz, C≡C—H), 1.60-0.25 (br m, 3H, BH$_3$).

$^{13}$C NMR (CDCl$_3$) δ: 161.4, 135.3, 333.6, 121.2, 116.5, 111.6, 77.2 (C≡C—H), 71.4 (C≡C—H), 55.9 (OCH$_3$), 17.2 (CH$_2$). The $^{13}$C assignments were confirmed by DEPT (distortionless enhancement by polarization transfer) experiment.

$^{31}$P NMR δ: 19.2 (d, J$_{PB}$=61 Hz)

Mass spectrometry (MS-MALDI) m/z: 285 [M−BH$_3$].

Example 3

Preparation of Pincer Ligands

A variety of pincer ligands were prepared using the Huisgen dipolar cycloaddition of azides and alkynes to yield triazoles. Precursors comprising an azidomethyl group, such as described in Example 1, were reacted with precursors comprising a propargyl (prop-2-ynyl) group, such as those described in Example 2, resulting in the formation of 1,4-substituted triazole pincer ligands.

Preparation of Protected Forms of Pincer Ligands:

Phosphine donor groups in the pincer ligand were obtained by using precursors comprising a protected form (phosphine oxide or phosphine-borane complex) of the phosphine group.

As an example, the synthesis of the protected form (borane complex) of the pincer ligand Compound 7 (see, FIG. 2) was performed as follows:

Synthesis of Protected Form of Compound 7:

To the alkyne precursor bis(phenyl)(prop-2-ynyl)phosphine borane complex (Compound 3a) (144 mg, 0.605 mmol) in 0.6 ml tetrahydrofuran was added the azide precursor azidomethyl phenyl sulfide (Compound 2) (100 mg, 0.605 mmol). In a separate vessel, CuSO$_4$·5H$_2$O (75.3 mg, 0.303 mmol) was dissolved in 0.6 ml distilled water. Upon addition of sodium ascorbate (599 mg, 3.025 mmol) to the aqueous mixture, the resulting dark brown mixture was quickly added to the reaction. The obtained reaction mixture was stirred at room temperature for 14 hours under nitrogen. The aqueous phase was extracted with ethyl acetate (3×10 ml) and the combined organic layers were washed with water (20 ml) and brine (20 ml). The organic phase was dried with anhydrous Na$_2$SO$_4$. The protected form (borane complex) of Compound 7 (139 mg, 80% yield) was obtained after evaporation as a white powder.

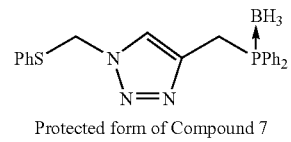

Protected form of Compound 7

$^{31}$P NMR (202 MHz): 14.5 (d).

$^1$H NMR (500 MHz, D$_2$O) δ: 7.69-7.65 (m, 4H), 7.36 (s, 1H, triazole-H), 7.08-7.07 (m, 2H), 6.97-6.87 (m, 6H), 6.87 (m, 3H), 4.77 (s, 2H, CH$_2$—S), 3.51 (d, 2H, J$_{CP}$=11 Hz, CH$_2$—P), 2.2-1.5 (br m, 3H, BH$_3$).

$^{13}$C NMR (500 MHz, D$_2$O) δ: 141.1, 134.2 (d, J$_{CP}$=9.23 Hz), 134.1, 133.8, 132.8 (d, J$_{CP}$=2.62 Hz), 131.0, 130.6, 130.4 (d, J$_{CP}$=9.56 Hz), 129.9, 129.8, 129.7, 129.6, 129.5, 129.3, 124.5 (d, J$_{CP}$=3.18 Hz), 54.67 (CH$_2$—S), 26.2 (d, J$_{CP}$=36.1 Hz, CH$_2$—P). The $^{13}$C assignments were confirmed by DEPT experiments.

Mass spectroscopy (MS-MALDI): m/z (%)=402 (55) [M−1]$^+$.

Using essentially the same procedures, the following protected forms of pincer ligands were obtained (see, FIG. 2):

Synthesis of protected form of Compound 5:

The azide precursor Compound 1 was reacted with the alkyne precursor Compound 3a according to the above-described procedures to obtain the following compound:

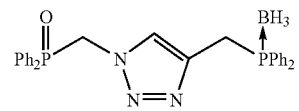

Protected form of Compound 5

$^1$H NMR (CDCl$_3$) δ: 7.64-7.61 (m, 10H), 7.43-7.36 (m, 11H), 5.11 (d, 2H, J$_{HP}$=6.9 Hz, N—CH$_2$—P), 3.66 (d, 2H, J$_{HP}$=11.1 Hz, C—CH$_2$—P), 1.5-0.3 (br m, 3H, BH$_3$).

$^{13}$C NMR (75 MHz) δ: 138.8 (d, J$_{CP}$=2.74 Hz), 132.5 (d, J$_{CP}$=2.45 Hz), 132.0 (d, J$_{CP}$=9.23 Hz), 131.0 (d, J$_{CP}$=1.91 Hz) 130.8 (d, J$_{CP}$=9.27 Hz), 128.6, 128.5 (d, J$_{CP}$=68.46 Hz), 128.4, 128.3, 127.6 (d, J$_{CP}$=20.65 Hz), 124.0 (d, J$_{CP}$=2.78 Hz), 49.8 (d, J$_{CP}$=70.36 Hz, CH$_2$—P), 24.0 (d, J$_{CP}$=35.83 Hz CH$_2$—P). The $^{13}$C assignments were confirmed by DEPT.

$^{31}$P NMR (121 MHz) δ: 23.62 (s, 1P, P═O) 14.78 (m, 1P, P—BH$_3$).

Synthesis of Protected Form of Compound 6:

The azide precursor Compound 1 was reacted with the alkyne precursor 2-ethynylpyridine according to the above-described procedures to obtain the following compound:

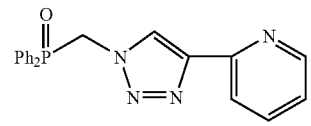

Protected form of Compound 6

$^1$H NMR (300 MHz, CDCl$_3$) δ: 8.58 (s, 1H), 8.44 (s, 1H), 8.02 (d, 1H), 7.81-7.47 (m, 11H, Ar), 7.21 (m, 2H), 5.32 (d, 2H, J$_{HP}$=7.2 Hz, CH$_2$—P).

$^{13}$C NMR (125 MHz) δ: 149.7, 149.4, 136.8, 133.0 (d, $J_{CP}$=2.7 Hz), 131.2 (d, $J_{CP}$=10.0 Hz), 129.3, 129.1 (d, $J_{CP}$=12.1 Hz), 123.4, 122.9, 120.2, 50.3 (d, $J_{CP}$=70.1 Hz, CH$_2$—P).

$^{31}$P NMR (120 MHz) δ: 24.4.

Mass spectroscopy (MS-ESI$^+$); m/z=361 [M+1].

Synthesis of Protected Form of Compound 8:

The azide precursor Compound 2 was reacted with the alkyne precursor Compound 3b according to the above-described procedures to obtain the following compound:

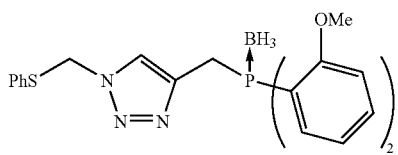

Protected form of Compound 8

$^1$H NMR (500 MHz, CDCl$_3$) δ: 7.80-7.75 (m, 2H, Ar) 7.56 (d, 1H), 7.05-7.03 (m, 4H Ar), 6.88-6.87 (M, 2H, Ar), 6.67-6.64 (m, 2H, Ar), 6.34-6.31 (m, 2H, Ar), 4.62 (s, 2H, CH$_2$—S), 4.26 (d, 2H, $J_{HP}$=12.5 Hz, CH$_2$—P), 3.18 (s, 6H, O-Me), 2.2-1.8 (br m, 3H, BH$_3$).

$^{13}$C NMR (125 MHz) δ: 163.1, 142.5, 134.4 (d, $J_{CP}$=10.9 Hz, 134.4 (d, $J_{CP}$=1.76 Hz), 133.8, 130.9, 129.7, 129.5, 129.3, 129.1, 124.0 (d, $J_{CP}$=2.98 Hz), 122.4 (d, $J_{CP}$=11.0 Hz), 119.0 (d, $J_{CP}$=54.6 Hz), 113.0 (d, $J_{CP}$=4.6 Hz), 56.8 (O-Me), 54.5 (CH$_2$—S), 25.1 (d, $J_{CP}$=50.0 Hz, CH$_2$—P). The $^{13}$C assignments were confirmed by DEPT.

$^{31}$P NMR (202 MHz) δ: 15.2 (m).

Mass spectroscopy (MS-ESI$^+$): m/z (%)=462 (100) [M=1]$^+$.

Deprotection of Phosphine Groups of Pincer Ligands:

Deprotection of Compound 5:

The phosphine oxide group of the protected form of Compound 5 was reduced as follows:

Trichlorosilane (934 μl, 9.25 mmol) and triethyl amine (2.60 ml, 18.5 mmol) were added to the protected form of Compound 5 (458.2 mg, 0.93 mmol) in toluene (30 ml) and dichloromethane (5 ml). This mixture was stirred in a closed, argon-filled flask and heated to 100° C. for 18 hours. The reaction mixture was then cooled and filtered through a pad of elite under inert conditions, resulting in the reduced phosphine. The obtained material was concentrated.

The phosphine-borane complex was then deprotected as follows:

The obtained material was re-dissolved in anhydrous tetrahydrofuran (10 ml). To this solution was added DABCO (124 mg, 1.11 mmol). The reaction mixture was then heated to 70° C. for 4 hours, resulting in full deprotection of the borane from the phosphine group. Remaining DABCO was removed by filtration through a short plug of silica. Washing with diethyl ether gave Compound 5 as a colorless solid (400 mg, 93% yield).

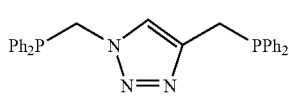

Compound 5

$^1$H NMR (500 MHz, CDCl$_3$) δ: 7.41-7.30 (m, 15H, Ar), 6.94 (s, 1H, triazole-H), 4.96 (d, 2H, $J_{HP}$=4.8 Hz, N—CH$_2$—P), 3.47 (s, 2H, C—CH$_2$—P).

$^{13}$C NMR (125 MHz) δ: 145.8 (d, $J_{CP}$=11.0 Hz), 139.5 (d, $J_{CP}$=14.0 Hz), 136.3 (d, $J_{CP}$=12.7 Hz), 134.7 (d, $J_{CP}$=13.9 Hz), 134.5 (d, $J_{CP}$=13.2 Hz), 131.5, 130.7, 130.6 (d, $J_{CP}$=3.8 Hz), 130.3, 130.2, 123.5, 55.8 (d, $J_{CP}$=19.6 Hz, N—CH$_2$—P), 27.1 (d, $J_{CP}$=14.9 Hz, C—CH$_2$—P). The $^{13}$C assignments were confirmed by DEPT.

$^{31}$P NMR (202 MHz) δ: −16.7.

Mass spectroscopy (MS-MALDI): m/z=488 [M+Na].

Elemental analysis: As the phosphine groups are air-sensitive, elemental percentages were calculated for the monophosphine oxide form: C, 69.85; H, 5.23; and di-oxide form: C, 67.60; H, 5.07. Found: C, 68.57; H, 5.98.

Using essentially the same procedures as described for deprotecting Compound 5, the following compounds were prepared:

Deprotection of Compound 6:

Compound 6 was obtained by reducing the phosphine oxide of the protected form, according to the above-described procedures.

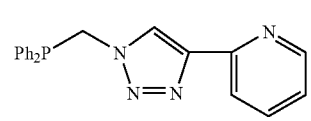

Compound 6

$^{31}$P NMR (120 MHz) δ: −13.4.

$^1$H NMR (300 MHz, CDCl$_3$) δ: 8.56 (d, 1H), 8.25 (d, 1H), 8.12 (s, 1H), 7.74 (t, 1H), 7.45-7.34 (m, 10H, Ar), 7.20 (m, 1H), 5.14 (d, 2H, $J_{HP}$=4.5 Hz, CH$_2$—P).

Deprotection of Compound 7:

Compound 7 was obtained by converting the phosphine-borane complex of the protected form to a phosphine group, according to the above-described procedures.

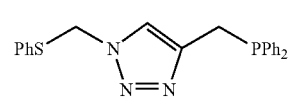

Compound 7

$^1$H NMR (500 MHz, CDCl$_3$) δ: 7.42-7.19 (m, 15H, Ar), 7.10 (s, 1H, triazole-H), 5.48 (s, 2H, CH$_2$—S), 3.50 (s, 2H, CH$_2$—P).

$^{13}$C NMR (125 MHz) δ: 14.2 (d, $J_{CP}$=10.8 Hz), 139.4 (d, $J_{CP}$=14.1 Hz), 134.6, 134.5, 134.1, 133.6, 131.2, 130.1, 130.4 (d, $J_{CP}$=7.5 Hz), 130.3, 122.8 (d, $J_{CP}$=6.9 Hz), 55.6 (CH$_2$—S), 27.1 (d, CH$_2$—P, $J_{CP}$=15.4 Hz). The $^{13}$C assignments were confirmed by DEPT.

$^{31}$P NMR (202 MHz) δ: −16.68.

Mass spectroscopy (MS-MALDI): m/z=390 [M+1].

Elemental analysis: Calculated C, 67.85; H, 5.18. Found: C, 67.05; H, 5.69.

Deprotection of Compound 8:

Compound 8 was obtained by converting the phosphine-borane complex of the protected form to a phosphine group, according to the above-described procedures.

Compound 8

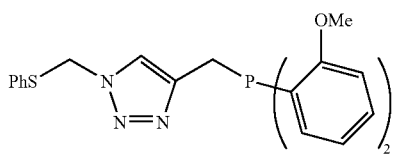

$^{31}$P NMR (202 MHz) δ: −33.7.

$^1$H NMR (300 MHz, CDCl$_3$) δ: 7.25-7.08 (m, 9H), 7.07-6.78 (m, 5H), 5.39 (s, 2H, CH$_2$—S), 3.70 (s, 6H, O-Me), 3.52 (s, 2H, CH$_2$—P). $^{13}$C NMR (202 MHz) δ: 161.2 (d, J$_{CP}$=13 Hz), 145.7 (d, J$_{CP}$=11.9 Hz), 133.0, 132.9, 132.3, 130.2, 129.3, 128.4, 142.3 (d, J$_{CP}$=15.8 Hz), 120.9, 120.8, 110.1, 55.5 (O-Me), 51.1 (d, CH$_2$—S), 21.4 (d, CH$_2$—P, J$_{CP}$=14.7 Hz). The $^{13}$C assignments were confirmed by DEPT.

Mass spectroscopy (MS-ESI$^+$): m/z=488 [M+K].

Elemental analysis: Calculated for phosphine oxide form: C, 61.92; H, 5.20. Found: C, 61.75; H, 5.90.

Example 4

Preparation of Palladium Pincer Complexes

The preparation of exemplary palladium pincer complexes according to embodiments of the invention is depicted in FIG. 4.

Preparation of Compound 9:

Compound 5 (20 mg; 0.043 mmol), tetramethylethylenediamine(TMEDA)-PdCl$_2$ (12 mg; 0.043 mmol) and triethylamine (10 equivalents) were combined in 2 ml of dimethylformamide. The resulting solution was heated at 70° C. for 12 hours. The solvent was evaporated and the residue was washed with ether (3×3 ml) and extracted with toluene/tetrahydrofuran (3×3 ml). The combined extractions were evaporated, resulting in pure compound 9 in a yield of 78%.

Compound 9

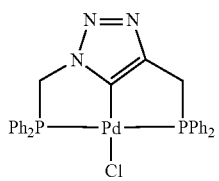

$^{31}$P{$^1$H} NMR (CDCl$_3$) 33.1 (d, J$_{PP}$=462.0 Hz); 23.4 (d, J$_{PP}$=462.0 Hz).

$^1$H NMR (CDCl$_3$): 7.30-6.79 (m, 20H, Ar), 4.86 (d, J$_{HP}$=4.7 Hz, 2H, N—CH$_2$—P), 3.68 (d, J$_{HP}$=5.2 Hz, 2H, C—CH$_2$—P).

$^{13}$C NMR (CDCl$_3$): 163.02 (bs, C$_{ipso}$), 132.61 (s, Ar), 132.55 (s, Ar), 132.48 (s, Ar), 132.40 (s, Ar), 132.31 (s, Ar), 131.33 (s, Ar), 130.72 (s, Ar), 130.31 (s, Ar), 128.88 (s, Ar), 128.70 (s, Ar), 128.56 (s, Ar), 128.40 (s, Ar), 128.12 (s, Ar), 67.25 (d, J$_{CP}$=30.0 Hz, N—CH$_2$—P), 52.34 (d, J$_{CP}$=39.5 Hz, C—CH$_2$—P) (assignment of $^{13}$C{$^1$H} NMR signals was confirmed by $^{13}$C DEPT).

Elemental analysis. Calculated: C, 55.46; H, 3.99. Found: C, 53.93; H, 3.78.

Using essentially the same procedures, the following complexes were prepared:

Compound 10:

Compound 10

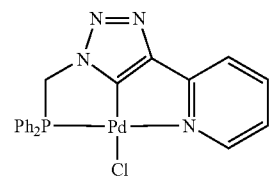

Compound 10 was prepared by complexing palladium to Compound 6.

$^{31}$P{$^1$H} NMR (CDCl$_3$): 21.4 (s).

$^1$H NMR (CDCl$_3$): 8.43-7.01 (m, 14H, Ar), 5.30 (d, J$_{HP}$=6.9 Hz, 2H, N—CH$_2$—P).

$^{13}$C NMR (CDCl$_3$): 153.92 (bs, C$_{ispo}$), 149.52 (s, Ar), 136.45 (s, Ar), 133.08 (s, Ar), 133.00 (s, Ar), 132.14 (s, Ar), 131.25 (d, J$_{CP}$=3.1 Hz), 129.04 (d, 2.4 Hz), 123.31 (s, Ar), 122.92 (s, Ar), 120.25 (s, Ar), 68.01 (d, J$_{CP}$=24.7 Hz, N—CH$_2$—P). Assignment of $^{13}$C{$^1$H} NMR signals was confirmed by $^{13}$C DEPT.

Elemental analysis: Calculated: C, 49.51; H, 3.32. Found: C, 49.36; H, 3.54.

Compound 11:

Compound 11

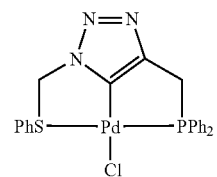

Compound 11 was prepared by complexing palladium to Compound 7.

$^{31}$P{$^1$H} NMR (CDCl$_3$) 24.17 (s).

$^1$H NMR (CDCl$_3$): 7.96-7.24 (m, 15H, Ar), 5.82 (s, 2H, CH$_2$—S), 3.84 (d, J$_{HP}$=11.3 Hz, 2H, CH$_2$—P).

$^{13}$C NMR (CDCl$_3$): 151.35 (d, J$_{CP}$=6.1 Hz C$_{ispo}$), 136.72 (s, Ar), 136.50 (s, Ar), 135.40 (d, J$_{CP}$=3.2 Hz, Ar), 135.01 (s, Ar), 132.76 (s, Ar), 132.34 (s, Ar), 132.10 (s, Ar), 131.61 (s, Ar), 131.40 (s, Ar), 130.33 (s, Ar), 130.11 (s, Ar), 127.04 (d, J$_{CP}$=13.2 Hz), 58.11 (CH$_2$—S), 30.12 (d, J$_{CP}$=33.1 Hz, CH$_2$—P). Assignment of $^{13}$C{$^1$H} NMR signals was confirmed by $^{13}$C DEPT.

Elemental analysis: Calculated: C, 49.83; H, 3.61. Found: C, 50.31; H, 4.09.

Compound 12:

Compound 12 was prepared by complexing palladium to Compound 8.

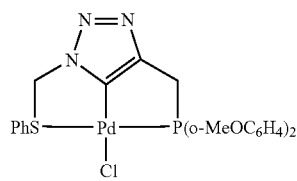

Compound 12

$^{31}P\{^1H\}$ NMR (CDCl$_3$) 25.35 (s).

$^1$H NMR (CDCl$_3$): 8.03-6.55 (m, 13H, Ar) 4.86 (s, 2H, CH$_2$—S), 4.51 (d, J$_{HP}$=7.4 Hz, 2H, CH$_2$—P), 3.42 (s, 6H, OCH$_3$). $^{13}$C NMR (CDCl$_3$): 166.25 (s, Ar), 156.51 (bs, C$_{ipso}$), 139.89 (s, Ar), 139.70 (s, Ar), 137.40 (s. Ar), 136(9 Ar), 134.06 (s, Ar), 132.84 (s, Ar), 132.61 (s, Ar), 132.43 (s, Ar), 127.11 (s, Ar), 125.45 (d, J$_{CP}$=9.2 Hz, Ar), 116.05 (d, J$_{CP}$=3.9 Hz, Ar), 59.82 (O—CH$_3$), 57.61 (CH$_2$—S), 28.13 (d, J$_{CP}$=38.3 Hz, CH$_2$—P) (assignment of $^{13}$C{$^1$H} NMR signals was confirmed by $^{13}$C DEPT).

Elemental analysis: Calculated: C, 48.83; H, 3.93. Found: C, 49.51; H, 4.78.

As shown in Table 1, $^{31}P\{^1H\}$ NMR showed quantitative formation of the complexes as a single product as compared to the corresponding free ligands.

TABLE 1

| Compound (free ligand) | $^{31}$P Shift (ppm) | Compound (palladium complex) | $^{31}$P Shift (ppm) |
|---|---|---|---|
| 5 | −16.7 | 9 | 33.1 (d), 23.4 (d) |
| 6 | −13.4 | 10 | 21.4 (s) |
| 7 | −16.7 | 11 | 24.2 (s) |
| 8 | −33.7 | 12 | 25.4 (s) |

Example 5

Structure of Pincer Ligand-Palladium Complexes

Compound 9 was characterized in solution by multinuclear NMR techniques. As described in Example 9, the $^{31}$P NMR spectrum of Compound 9 was shows two doublets at 33.1 and 23.4 ppm with a typical trans phosphorus-phosphorus coupling constant of 462.0 Hz. In the $^{13}$C NMR spectrum the ipso carbon gives rise to a broad signal centered at 163.0 ppm indicating a formed carbon-metal bond. Similar results were obtained from NMR analysis of Compounds 10-12, as further described in Example 4 hereinabove.

The molecular structure of Compound 9 was confirmed by X-ray analysis. Yellow crystals of Compound 9 suitable for single crystal X-ray analysis were obtained by slow diffusion of diethyl ether to a dichloromethane solution.

As shown in FIG. 5, the palladium atom is located in the centre of a distorted square planar structure with the chloride group occupying a position trans to the carbon atom of the triazole. The two phosphine groups are located in mutual trans positions with a P—Pd—P angle of 157.02.

CCDC 673968 contains the supplementary crystallographic data. These crystallographic data can be obtained free of charge from the Cambridge Crystallographic Data Centre via www.ccdc.cam.ac.uk/data_request/cif.

These results indicate that that the triazole-based pincer ligands are tridentate ligands, as the metal binds not only to the donor groups attached to the triazole, but also to the carbon atom of the triazole.

Example 6

Catalytic Efficiency of Complexes

Facile combinatorial access to a novel family of pincer-ligands and their corresponding metal complexes opens the door to rapid and convenient screening of these systems in various catalytic transformations. With numerous palladium complexes in hand, the ligand influence on catalytic activity in the Heck reaction was examined. The Heck reaction examined is depicted in Scheme 1 hereinbelow.

Scheme 1

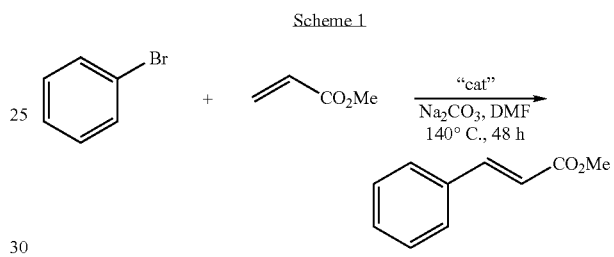

6 mmol of methyl acrylate was added to 5 mmol of bromobenzene in dimethylformamide, followed by the addition of an equimolar amount of sodium carbonate. The catalyst was added in amounts of 3.5×10$^{-5}$ mmol of complex (7×10$^{-4}$ mol %). The resulting mixture was stirred at 140° C. while the reaction progression was followed by gas chromatography. Results of these experiments are presented in Table 2.

TABLE 2

| Compound | Yield [%] | TON (turnover number) |
|---|---|---|
| 9 | 94 | 134,000 |
| 10 | 88 | 125,000 |
| 11 | 29 | 42,000 |
| 12 | 5 | 6,900 |

As shown in Table 2, Compounds 9 and 10 are incredibly efficient catalysts for the Heck reaction. Interestingly, based upon yield and conversion, Compound 9 is among the most active and efficient catalysts for Heck coupling with aryl bromides. Compound 9 mediates the reaction of bromobenzene with methyl acrylate giving a 94% yield and an observed TON (turnover number) of 134,000 after 48 hours.

These results indicate that preparation of pincer type tridentate ligands as described hereinabove is highly advantageous for combinatorial synthesis of non-trivial ligands from relatively simple building blocks.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A compound of the general Formula I:

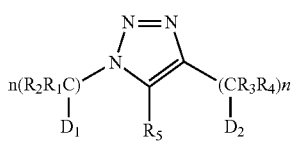

Formula I wherein:

n is an integer from 1 to 4;

$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, nitro and cyano;

$R_5$ is a leaving group capable of being dissociated so as to form a carbanion;

$D_1$ is an electron donating group of the general Formula IIa:

$Z_1 Z_2 Xa$;  Formula IIa and $D_2$ is an electron donating group of the general Formula IIb:

$Z_3 Z_4 Xb$;  Formula IIb whereas:

Xa and Xb are each independently an electron donating atom; and $Z_1$, $Z_2$, $Z_3$ and $Z_4$ are each independently absent or a substituent selected from the group consisting of substituted or non-substituted aryl, substituted or non-substituted alkyl, substituted or non-substituted alkoxy and substituted or non-substituted aryloxy, or, alternatively, at least two of $Z_1$, $Z_2$, $R_1$ and $R_2$ and/or at least two of $Z_3$, $Z_4$, $R_3$ and $R_4$ from together a five- or six-membered heteroalicyclic or heteroaromatic ring, wherein each of said electron donating atoms Xa and Xb is independently selected from the group consisting of phosphorous, sulfur, nitrogen and carbon, said carbon being a carbene that forms a part of a N-heteroalicyclic or a N-heteroaryl, and wherein at least one of said $D_1$ and $D_2$ having said general Formula IIa or IIb, respectively, is being such that said electron donating atom is phosphorus and either said $Z_1$ and $Z_2$ or said $Z_3$ and $Z_4$ substituents of said phosphorous are each independently a substituted or non-substituted aryl.

2. The compound of claim 1, wherein $R_1$-$R_5$ are each hydrogen.

3. The compound of claim 1, wherein n equals 1.

4. The compound of claim 2, wherein n equals 1.

5. The compound of claim 1, wherein Xa and Xb are each phosphorus.

6. The compound of claim 1, wherein Xa is phosphorus and Xb is nitrogen.

7. The compound of claim 1, wherein Xa is sulfur and Xb is phosphorus.

8. The compound of claim 7, wherein $Z_3$ and $Z_4$ are each aryl.

9. The compound of claim 7, wherein $Z_1$ is aryl and $Z_2$ is absent.

10. The compound of claim 6, wherein $Z_1$ and $Z_2$ are each aryl.

11. The compound of claim 5, wherein each of $Z_1$, $Z_2$, $Z_3$ and $Z_4$ is independently a substituted or non-substituted aryl.

12. The compound of claim 1, being selected from the group consisting of:

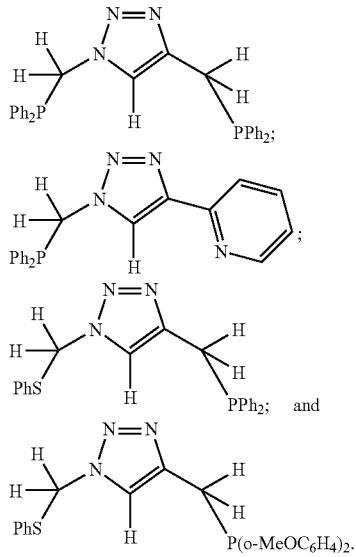

13. A process of preparing the compound of claim 1, the process comprising:

reacting, via a 1,3-dipolar cycloaddition reaction, a compound having general Formula IIIa:

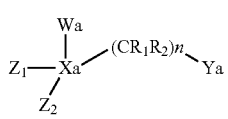

Formula IIIa with a compound having general Formula IIIb:

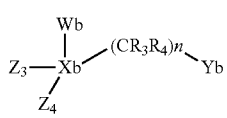

Formula IIIb wherein:

Wa and Wb are each independently a protecting group or absent;

Ya is a —$N_3$ group;

Yb is a—$R_5$ group;

n is said integer from 1 to 4;

$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, halogen, nitro and cyano;

R₅ is said leaving group;

Xa and Xb are each independently said electron donating atom; and $Z_1$, $Z_2$, $Z_3$ and $Z_4$ are each independently absent or said substituent selected from the group consisting of substituted or non-substituted aryl, substituted or non-substituted alkyl, substituted or non-substituted alkoxy and substituted or non-substituted aryloxy, or, alternatively, at least two of $Z_1$, $Z_2$, $R_1$ and $R_2$ and/or at least two of $Z_3$, $Z_4$, $R_3$ and $R_4$ from together a five- or six-membered heteroalicyclic or heteroaromatic ring, wherein each of said electron donating atoms Xa and Xb is independently selected from the group consisting of phosphorous, sulfur, nitrogen and carbon, said carbon being a carbene that forms a part of a N-heteroalicyclic or a N-heteroaryl, and wherein at least one of said $D_1$ and $D_2$ having said general Formula IIa or IIb, respectively, is being such that said electron donating atom is phosphorus and either said $Z_1$ and $Z_2$ in or said $Z_3$ and $Z_4$ substituents of said phosphorous are each independently a substituted or non-substituted aryl.

14. The process of claim 13, wherein said cycloaddition reaction is performed in the presence of a copper (I) catalyst.

15. The process of claim 14, wherein said cycloaddition reaction is performed at room temperature.

16. The process of claim 13, wherein said cycloaddition reaction is the "click" reaction.

17. The process of claim 13, wherein at least one of said Wa and Wb is said protecting group, the process further comprising, subsequent to said reacting:

removing said protecting group.

18. The process of claim 13, being for forming a combinatorial library of tridentate ligands having said general Formula I.

19. A combinatorial library of tridentate ligands, the library comprising a plurality of compounds having the general Formula I:

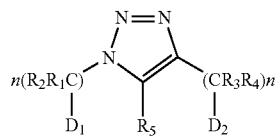

Formula I wherein:

n is an integer from 1 to 4;

$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, nitro and cyano;

$R_5$ is a leaving group capable of being dissociated so as to form a carbanion;

$D_1$ is an electron donating group of the general Formula IIa:

$Z_1Z_2Xa$          Formula IIa;

and $D_2$ is an electron donating group of the general Formula IIb:

$Z_3Z_4Xb$          Formula IIb;

whereas:

Xa and Xb are each independently an electron donating atom; and $Z_1$, $Z_2$, $Z_3$ and $Z_4$ are each independently absent or a substituent selected from the group consisting of substituted or non-substituted aryl, substituted or non-substituted alkyl, substituted or non-substituted alkoxy and substituted or non-substituted aryloxy, or, alternatively, at least two of $Z_1$, $Z_2$, $R_1$ and $R_2$ and/or at least two of $Z_3$, $Z_4$, $R_3$ and $R_4$ from together a five- or six-membered heteroalicyclic or heteroaromatic ring, wherein each of said electron donating atoms Xa and Xb is independently selected from the group consisting of phosphorous, sulfur, nitrogen and carbon, said carbon being a carbene that forms a part of a N-heteroalicyclic or a N-heteroaryl, and wherein at least one of said $D_1$ and $D_2$ having said general Formula IIa or IIb, respectively, is being such that said electron donating atom is phosphorus and either said $Z_1$ and $Z_2$ or said $Z_3$ and $Z_4$ substituents of said phosphorus are each independently a substituted or non-substituted aryl, said compounds being different from one another in at least one of said electron donating groups D1 and D2 and/or at least one of said n and $R_1$-$R_5$.

20. An organometallic complex comprising a metal and the compound of claim 1 serving as a tridentate ligand being in complex with said metal, the complex having general Formula V:

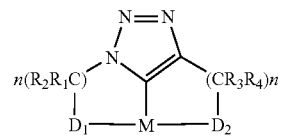

Formula V wherein:

n is said integer from 1 to 4;

$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, halogen, nitro and cyano;

M is a transition metal;

$D_1$ is said electron donating group of the general Formula IIa:

$Z_1Z_2Xa$          Formula IIa;

and $D_2$ is an electron donating group of the general Formula IIb:

$Z_3Z_4Xb$          Formula IIb, whereas:

Xa and Xb are each independently said electron donating atom; and $Z_1$, $Z_2$, $Z_3$ and $Z_4$ are each independently absent or a substituent selected from the group consisting of substituted or non-substituted aryl, substituted or non-substituted alkyl, substituted or non-substituted alkoxy and substituted or non-substituted aryloxy, or, alternatively, at least two of $Z_1$, $Z_2$, $R_1$ and $R_2$ and/or at least two of $Z_3$, $Z_4$, $R_3$ and $R_4$ from together a five- or six-membered heteroalicyclic or heteroaromatic ring, wherein each of said electron donating atoms Xa and Xb is independently selected from the group consisting of phosphorous, sulfur, nitrogen and carbon, said carbon being a carbene that forms a part of a N-heteroalicyclic or a N-heteroaryl, and wherein at least one of said $D_1$ and $D_2$ having said general Formula IIa or IIb, respectively, is being such that said electron donating atom is phosphorus and either said $Z_1$ and $Z_2$ or said $Z_3$ and $Z_4$ substituents of said phosphorus are each independently a substituted or non-substituted aryl.

21. The complex of claim 20, wherein M is selected from the group consisting of palladium, platinum, rhodium, zirconium, ruthenium, iridium, nickel, iron, and osmium, each optionally further comprising an additional ligand.

22. A process of preparing the organometallic complex of claim 20, the process comprising contacting a salt or a complex of said metal with a compound having general Formula I:

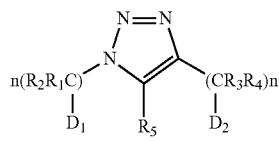

Formula I
wherein:
n is an integer from 1 to 4;
$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, nitro and cyano;
$R_5$ is a leaving group capable of being dissociated so as to form a carbanion;
$D_1$ is an electron donating group of the general Formula IIa:

$Z_1Z_2Xa$      Formula IIa;

and
$D_2$ is an electron donating group of the general Formula IIb:

$Z_3Z_4Xb$      Formula IIb;

whereas:
Xa and Xb are each independently an electron donating atom; and
$Z_1$, $Z_2$, $Z_3$ and $Z_4$ are each independently absent or a substituent selected from the group consisting of substituted or non-substituted aryl, substituted or non-substituted alkyl, substituted or non-substituted alkoxy and substituted or non-substituted aryloxy, or, alternatively, at least two of $Z_1$, $Z_2$, $R_1$ and $R_2$ and/or at least two of $Z_3$, $Z_4$, $R_3$ and $R_4$ from together a five- or six-membered heteroalicyclic or heteroaromatic ring,
wherein each of said electron donating atoms Xa and Xb is independently selected from the group consisting of phosphorous, sulfur, nitrogen and carbon, said carbon being a carbene that forms a part of a N-heteroalicyclic or a N-heteroaryl,
and wherein at least one of said $D_1$ and $D_2$ having said general Formula IIa or IIb, respectively, is being such that said electron donating atom is phosphorus and either said $Z_1$ and $Z_2$ or said $Z_3$ and $Z_4$ substituents of said phosphorus are each independently a substituted or non-substituted aryl.

23. The process of claim 22, wherein said contacting is performed under basic conditions.

24. A combinatorial library of organometallic complexes, the library comprising a plurality of organometallic complexes having general Formula V:

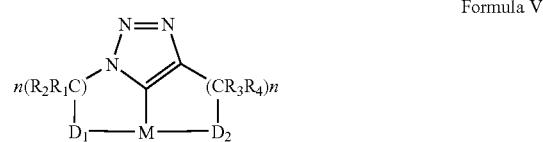

wherein:
n is said integer from 1 to 4;
$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, halogen, nitro and cyano;
M is said transition metal; and
$D_1$ is said electron donating group of the general Formula IIa:

$Z_1Z_2Xa$      Formula IIa;

and
$D_2$ is an electron donating group of the general Formula IIb:

$Z_3Z_4Xb$      Formula IIb;

whereas:
Xa and Xb are each independently said electron donating atom; and
$Z_1$, $Z_2$, $Z_3$ and $Z_4$ are each independently absent or a substituent selected from the group consisting of substituted or non-substituted aryl, substituted or non-substituted alkyl, substituted or non-substituted alkoxy and substituted or non-substituted aryloxy, or, alternatively, at least two of $Z_1$, $Z_2$, $R_1$ and $R_2$ and/or at least two of $Z_3$, $Z_4$, $R_3$ and $R_4$ from together a five- or six-membered heteroalicyclic or heteroaromatic ring,
wherein each of said electron donating atoms Xa and Xb is independently selected from the group consisting of phosphorous, sulfur, nitrogen and carbon, said carbon being a carbene that forms a part of a N-heteroalicyclic or a N-heteroaryl,
and wherein at least one of said $D_1$ and $D_2$ having said general Formula IIa or IIb, respectively, is being such that said electron donating atom is phosphorus and either said $Z_1$ and $Z_2$ or said $Z_3$ and $Z_4$ substituents of said phosphorus are each independently a substituted or non-substituted aryl,
said complexes being different from one another in at least one of said metal, said electron donating groups D1 and D2 and at least one of said n and $R_1$-$R_5$.

25. A method of identifying a candidate organometallic complex for catalyzing a chemical reaction, the method comprising:
screening the combinatorial library of claim 24, by determining a catalytic activity of at least a portion of said plurality of organometallic complexes in said chemical reaction, thereby identifying the candidate organometallic complex.

* * * * *